(12) United States Patent
Uchida et al.

(10) Patent No.: US 7,967,900 B2
(45) Date of Patent: Jun. 28, 2011

(54) AIR FILTERING APPARATUS

(75) Inventors: Yoichi Uchida, Tochigi (JP); Hiroaki Usui, Gunma (JP); Nobuhiro Ogura, Gunma (JP); Toru Arakawa, Gunma (JP)

(73) Assignee: Sanyo Electric Co., Ltd., Moriguchi, Osaka (JP)

( * ) Notice: Subject to any disclaimer, the term of this patent is extended or adjusted under 35 U.S.C. 154(b) by 756 days.

(21) Appl. No.: 11/927,264

(22) Filed: Oct. 29, 2007

(65) Prior Publication Data

US 2008/0098899 A1    May 1, 2008

(30) Foreign Application Priority Data

Oct. 30, 2006    (JP) .................... 2006-293452
Oct. 30, 2006    (JP) .................... 2006-293505
Oct. 30, 2006    (JP) .................... 2006-293610

(51) Int. Cl.
B01D 47/00    (2006.01)

(52) U.S. Cl. ............. 96/234; 96/296; 96/265; 96/263; 96/274; 95/211; 95/214

(58) Field of Classification Search .......... 95/24, 149, 95/408–412, 234, 245, 273, 277, 211, 214; 96/243, 255, 234, 296, 263, 265, 274

See application file for complete search history.

(56) References Cited

U.S. PATENT DOCUMENTS

| | | | | |
|---|---|---|---|---|
| 1,972,109 A | * | 9/1934 | Riebel, Jr. et al. | 261/127 |
| 2,502,137 A | * | 3/1950 | Fleisher | 95/13 |
| 4,943,002 A | * | 7/1990 | Fraher | 232/43.1 |
| 5,354,515 A | | 10/1994 | Ushimaru | |
| 5,507,543 A | * | 4/1996 | Shefflin | 294/146 |
| 5,944,978 A | * | 8/1999 | Okazaki | 205/701 |
| 7,407,624 B2 | * | 8/2008 | Cumberland et al. | 422/28 |
| 7,754,157 B2 | * | 7/2010 | Tomioka et al. | 422/121 |
| 7,779,868 B2 | * | 8/2010 | Higashino et al. | 138/39 |
| 2003/0024828 A1 | * | 2/2003 | Kondo et al. | 205/742 |
| 2003/0056648 A1 | | 3/2003 | Fornai et al. | |
| 2007/0151338 A1 | * | 7/2007 | Benner et al. | 73/317 |

FOREIGN PATENT DOCUMENTS

| | | |
|---|---|---|
| EP | 1 507 123 A2 | 2/2005 |
| JP | 5-340556 A | 12/1993 |
| JP | 07-158891 A | 6/1995 |
| JP | 08-312993 A * | 11/1996 |

(Continued)

OTHER PUBLICATIONS

European Search Report dated Aug. 31, 2010, issued in corresponding European Patent Application No. 07021199.0.

*Primary Examiner* — Duane Smith
*Assistant Examiner* — Ives Wu
(74) *Attorney, Agent, or Firm* — Westerman, Hattori, Daniels & Adrian, LLP

(57) ABSTRACT

In an air filtering apparatus for generating electrolytic water, infiltrating the electrolytic water into a gas-liquid contact member, and blowing air to the gas-liquid contact member by an air blowing fan, thereby filtering air, including a drain pipe for discharging the electrolytic water and a drain tank for receiving and stocking the electrolytic water discharged from the drain pipe which are mounted in a housing, the drain tank has a vertical tank body and disposed so as to be taken in and out through the front surface of the housing.

5 Claims, 19 Drawing Sheets

FOREIGN PATENT DOCUMENTS

| | | | |
|---|---|---|---|
| JP | 08312993 | * | 11/1996 |
| JP | 2002-181358 | * | 6/2002 |
| JP | 2002-181358 A | | 6/2002 |
| JP | 2002181358 | * | 6/2002 |
| JP | 2003-001043 A | | 1/2003 |
| JP | 2004245474 A | * | 9/2004 |
| JP | 2005484525 | * | 7/2005 |
| JP | 2005-282902 A | | 10/2005 |

* cited by examiner

AIR FILTERING APPARATUS

INCORPORATION BY REFERENCE

The present application claims priority under 35 U.S.C. §119 to Japanese Patent Application Nos. 2006-293452, 2006-293505, and 2006-293610 filed on Oct. 30, 2006. The contents of the applications are incorporated herein by reference in its entirety.

BACKGROUND OF THE INVENTION

1. Field of the Invention

The present invention relates to an air filtering apparatus that can remove microorganisms floating in the air such as bacteria, virus, fungus, etc. (hereinafter referred to as "virus, etc.").

2. Description of the Related Art

There has been known a filtering apparatus for electrolyzing tap water to generate electrolytic water and remove virus, etc. floating in the air by using this electrolytic water (for example, JP-A-2002-181358). According to this filtering apparatus, electrolytic water is supplied to a humidifying element formed of non-woven cloth or the like to bring virus, etc. in the air into contact with the electrolytic water on the humidifying element and inactivate the virus, etc., thereby filtering the air.

In the above filtering apparatus, etc., the electrolytic water supplied to the humidifying element is directly discharged to the outside of the apparatus or circulated for reuse. In any case, it is preferable to discharge the electrolytic water at a proper timing. This is because high air filtering performance can be maintained by exchanging water dissolved with odor components, etc. in the air by fresh water. It is expected that the above filtering apparatus, etc. are frequently used over a long term, and thus it is desired that the user's operation to discharge electrolytic water is simple and easy.

Furthermore, this type of filtering apparatuses has a problem that an air blowing (air flowing) amount to the humidifying element has an uneven distribution and thus sufficient filtering performance cannot be exercised, and also a problem that the water quality of tap water is varied in accordance with a district where the tap water is used and thus the concentration of active oxygen specifies contained in generated electrolytic water is different, so that it is impossible to obtain electrolytic water containing a predetermined concentration of active oxygen specifies in the electrolysis process.

SUMMARY OF THE INVENTION

Therefore, the present invention has been implemented in views of the foregoing situation, and has an object to provide an air filtering apparatus from which electrolytic water can be simply and easily discharged.

Another object of the present invention is to provide an air filtering apparatus whose air filtering performance can be enhanced by making uniform a distribution of an air blowing amount to a humidifying element (gas-liquid contact member).

Further object of the present invention is to provide an air filtering apparatus in which a current supply state in an electrolysis process is properly changed in accordance with the water quality of water being used.

In order to attain the above objects, according to a first aspect of the present invention, an air filtering apparatus for generating electrolytic water, infiltrating the electrolytic water into a gas-liquid contact member, and blowing air to the gas-liquid contact member by an air blowing fan, thereby filtering air, comprises a drain pipe for discharging the electrolytic water and a drain tank for receiving and stocking the electrolytic water discharged from the drain pipe which are mounted in a housing, wherein the drain tank has a vertical tank body and disposed so as to be taken in and out through the front surface of the housing.

According to this construction, the electrolytic water infiltrated into the gas-liquid contact member can be discharged from the drain pipe to the drain tank. Furthermore, the drain tank is designed to have the vertical (longer in the lengthwise direction than in the widthwise direction), and disposed so that it can be taken in and out through the front surface of the housing, so that the drain tank can be simply and easily taken out from the air filtering apparatus. Therefore, water stocked in the drain tank can be easily discarded. Furthermore, the tank body of the drain tank is designed as a vertical type (longer in the lengthwise direction than in the widthwise direction), and thus the drain tank can be easily disposed in an empty space inside the housing. Accordingly, there can be implemented an air filtering apparatus in which the drain tank is disposed at such a position that it can be easily taken out from the front surface of the housing, whereby a work required for drainage can be simply and easily performed.

In the present invention, it is preferable that the drain tank is provided with a grip portion which is swingably secured to the tank body, and the grip portion is movable within the swingable range so that the grip portion can be located at least in front of the tank body and at the upper side of the tank body.

According to this construction, the grip portion of the drain tank is movable to the positions at the front side of the tank body and at the upper side of the tank body. Therefore, if the grip portion is located in front of the tank body under the state that the drain tank is loaded in the housing, the grip portion can be easily taken in and out by grasping the grip portion and pulling out the drain tank from the front surface of the housing, for example, and also the height of the drain tank when the drain tank is loaded in the housing can be suppressed. Furthermore, if the grip portion is located at the upper side of the drain tank under the state that the drain tank is taken out from the housing, the drain tank can be easily handled while the grip portion is grasped by a hand. Accordingly, the handling work of the drain tank can be easily performed without losing the storage space performance of the drain tank.

Furthermore, in the above invention, a lid having a drain port may be secured to the tank body so that water in the tank body can be discharged from the drain port, and the grip portion may be equipped with a closing member for closing the drain port under the state that the grip portion is located at one end of the swingable range.

According to the above construction, the lid having the drain port is secured to the drain tank, and the drain port is closed by the closing member of the grip portion of the drain tank. Therefore, under such a water non-discharge state as a state that the drain tank is loaded in the housing or the like, for example, the water can be prevented from flowing out from the drain tank by closing the drain port. Furthermore, by swinging the grip portion as occasion demands, the water can be discharged from the drain tank. Accordingly, unintentional flow-out of water from the drain tank can be surely prevented without losing the easiness of the work required for the drainage.

In the present invention, the lid may be provided with a drain receiver for receiving water dropped from the drain pipe and leading the water into the tank body.

According to this construction, the drain receiver for leading the water from the drain pipe into the tank body is provided to the lid, whereby water leakage and water scattering in the housing can be prevented.

Furthermore, the air filtering apparatus according to the present invention may be further equipped with a displaceable member which is displaced in accordance with the water level in the tank body, and a detecting unit for detecting the displacement of the displaceable member.

According to this construction, the water level in the tank body can be detected and thus over-flow of water from the drain tank can be surely prevented.

Furthermore, the displaceable member is equipped with a float portion floating in the water in the tank body, and a magnet portion displaceable integrally with the float portion. The detecting unit detects approach of the magnet portion to the lid, and when the approach of the magnet portion is detected by the detecting means, discharge of the water in the tank body is guided.

According to this construction, by a simple construction having an extremely lower risk of trouble, it can be surely detected that the water level in the tank body rises up to a predetermined level or more, and thus over-flow of water from the drain tank can be surely prevented. Furthermore, when the water rising in the tank body is detected, a guidance for drainage is given to a user. Therefore, the user can use the air filtering apparatus without paying his/her attention to the water level of the drain tank and the load required to manage the air filtering apparatus can be greatly reduced.

In the present invention, the drain pipe may be branched from an electrolytic water circulating unit for circulating/supplying electrolytic water to the gas-liquid contact member and discharges the electrolytic water.

In this case, in the air filtering apparatus using electrolytic water in a circulation style, a high air filtering effect can be maintained by properly discharging electrolytic water and replacing it with fresh water, and also the work of discarding the electrolytic water is extremely simple. Accordingly, the air filtering apparatus in which the high air filtering effect can be maintained can be implemented without increasing the load imposed on the user.

Furthermore, according to a second aspect of the present invention, an air filtering apparatus having a gas-liquid contact member provided in the housing so as to be erected in the housing, an electrolytic water generating unit for generating electrolytic water supplied to the gas-liquid contact member, and an air blowing fan for blowing air to the gas-liquid contact member, wherein an air flow passage for guiding air blown out from the air blowing fan to the gas-liquid contact member is formed in the housing, and a suppress member for suppressing an air flow amount at a side of the gas-liquid contact member which is farther from the air blowing fan is disposed in the air flow passage.

According to this construction, the air flow amount at the side of the gas-liquid contact member which is farther from the air blowing fan is suppressed by the suppressing member disposed in the air flow passage, whereby the air flow amount at the side of the gas-liquid contact member which is nearer to the air blowing fan is relatively increased. Therefore, unevenness of the air flow amount in the gas-liquid contact member can be suppressed. Accordingly, air can be substantially uniformly blown to the gas-liquid crystal member, and thus the air filtering capability of the gas-liquid contact member can be sufficiently exercised.

In this case, the air flow passage guides the air blown out upwardly from the air blowing fan disposed at the lower side of the gas-liquid contact member to the gas-liquid contact member, and the suppressing member may be configured to suppress the air flow amount at the upper portion of the gas-liquid contact member in the air flow passage. According to this construction, the air flow amount at the upper portion of the gas-liquid contact member is suppressed, whereby the air flow amount at the lower portion of the gas-liquid contact member is relatively increased, so that unevenness of the air flow amount in the gas-liquid contact member can be suppressed. Accordingly, the air can be substantially uniformly blown to the gas-liquid contact member, and thus the air filtering performance of the gas-liquid contact member can be sufficiently exercised.

In this case, the suppressing member may be located in the air flow passage so as to face the upper portion of the gas-contact member. According to this construction, the air flow amount at the upper portion of the gas-liquid contact member is suppressed, and thus the air flow amount at the lower portion of the gas-liquid contact member is relatively increased, so that unevenness of the air flow amount in the gas-liquid contact member can be suppressed.

Furthermore, the suppressing member may have a first flow dividing plate disposed so as to face the upper end portion of the gas-liquid contact member and a second flow dividing late disposed at a lower position than the first flow dividing plate, and the first and second flow dividing plates may be disposed so as to be inclined downwardly to the gas-liquid contact member.

Still furthermore, according to a third aspect of the present invention, an air filtering apparatus comprises a housing having an air suction port and an air blow-out port, an air blower for forming an air flow passage extending from the air suction port to the air blow-out port in the housing, an air filtering unit that is disposed in the air flow passage and brings electrolytic water into contact with air supplied through the air flow passage to filter the air, an electrolytic water generator having at least a pair of electrodes for electrolyzing predetermined water to generate the electrolytic water, and a controller that is disposed in an electrical component box and controls a current supply state of the electrodes, the air blower, the air filtering unit, the electrolytic water generator and the controller being mounted in the housing, wherein the controller is provided with an operating unit for renewing the current supply state of the electrodes, and the electrical component box is provided with an opening through which the operating unit is exposed to the outside of the electrical component box.

According to this construction, the air flow passage extending from the air suction port to the air blow-out port is formed in the housing by the air blower. In the air filtering unit disposed on the air flow passage, air supplied through the air flow passage is filtered by the electrolytic water. The electrolytic water generator has at least a pair of electrodes, and the predetermined water is electrolyzed to generate the electrolytic water. The current supply state of the electrodes in the electrolytic water generator is controlled by the controller. The controller is provided with the operating unit for renewing the current supply state described above. The operating unit is exposed to the outside of the electrical component box through the opening formed in the electrical component box in which the controller is accommodated. Accordingly, the current supply state in the electrolysis process can be easily changed without opening the electrical component box. Furthermore, the electrical component box is disposed in the housing, and thus the current supply state of the electrodes can be prevented from being carelessly changed by a user or the like.

In the thus-constructed air filtering apparatus, the operating unit is preferably configured so that the current supply state of the electrodes is stepwise changeable to any one of preset current supply states of plural stages by rotating the operating unit.

According to this construction, the user, etc. can easily change the current supply state to any one of the preset plural current supply stages by rotating the operating unit.

Furthermore, in the above air filtering apparatus, it is preferable that the housing has a freely-detachable face panel and the electrical component box is disposed in the housing so that the operating unit is exposed to the outside when the face panel is detached.

According to this construction, when the face panel is detached, the electrical component box is disposed in the housing so that the operating unit is exposed to the outside. Therefore, by detaching the face panel, it is possible to easily change the current supply state of the electrodes by manipulating the operating unit. Furthermore, by attaching the face panel, the operating unit can be prevented from being exposed to the outside, and the current supply state of the electrodes can be prevented from being carelessly changed by the user or the like.

Furthermore, in the above air filtering apparatus, it is preferable that the electrical component box is provided with a flange portion projecting to the outside of the electrical component box and the operating unit is provided at the lower side of the flange portion.

According to this construction, the electrical component box is provided with the flange portion projecting to the outside of the electrical component box, and the operating unit is provided below this flange portion. The operating unit is disposed so as to be exposed to the outside of the electrical component box through the opening formed in the electrical component box, so that water or the like can be prevented from invading through the opening into the electrical component box by the flange portion.

Furthermore, in the above air filtering apparatus, the operating unit is preferably configured to change a power amount to be supplied to the electrodes.

The operating unit may change a time for which current is supplied between the electrodes. Furthermore, the operating unit may change a current amount flowing between the electrodes.

BRIEF DESCRIPTION OF THE DRAWINGS

FIGS. 8A and 8B are diagrams showing an aspect of supplying electrolytic water, wherein FIG. 8A is a schematic diagram showing the construction of an air filtering mechanism, and FIG. 8B is a diagram showing the detailed construction of an electrolytic bath;

FIGS. 12A and 12B are perspective views showing the construction of the drain tank, wherein FIG. 12A shows the drain tank taken out from the housing, and FIG. 12B shows a state that the drain tank is grasped by a hand;

DETAILED DESCRIPTION OF THE PREFERRED EMBODIMENTS

Preferred embodiments according to the present invention will be described hereunder with reference to the accompanying drawings.

Figure 1:
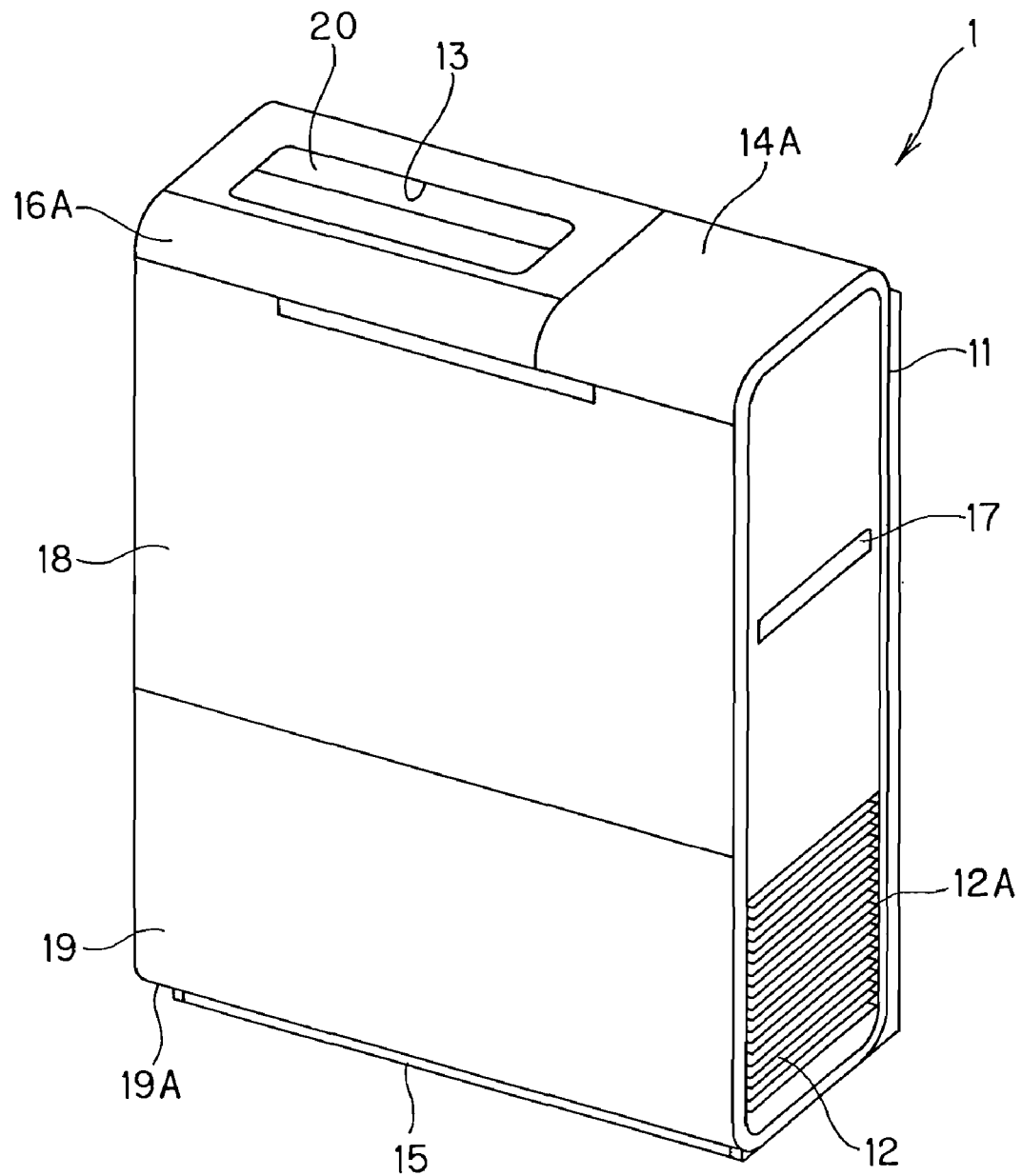
FIG. 1 is a perspective view showing the outlook of an air filtering apparatus according to an embodiment of the present invention.

FIG. 1 is a perspective view showing the outlook of an air filtering apparatus 1 according to an embodiment to which the present invention is applied.

As shown in FIG. 1, the air filtering apparatus 1 has a box-shaped housing 11 which is designed as a vertical type (longer in the lengthwise direction than in the widthwise direction), for example, in a substantially rectangular parallelepiped shape, and it is mounted on the floor, for example. An air suction port 12 for sucking air into the housing 11 is formed at the lower portion of at least one of both the side surfaces of the housing 11, and the air suction port 12 is provided with a suction grille 12A having a plurality of elongated vanes which are arranged in the horizontal direction so as to be in parallel to one another, for example. Furthermore, an air suction port 15 is also formed at the lower end portion of the front surface of the housing 11.

Furthermore, an air blow-out port 13 is formed in the top surface of the housing 11, and it is provided with a louver 20 for changing the air blowing direction. The louver 20 is configured to close the air blow-out port 13 when the operation of the air filtering apparatus is stopped.

The air filtering apparatus 1 sucks air through the suction port 12 and the air suction port 15 to filter the air. The air concerned may be indoor air in a room where the air filtering apparatus is mounted or outdoor air. The filtered air is discharged from the air blow-out port 13 into the room, thereby cleaning the indoor air.

On the top surface of the housing 11 are provided an operation lid (opening/closing lid) 16A disposed at the front side of the air-blow port 13 and a tank opening/closing lid 14A disposed in juxtaposition with (for example, at the right side in front view) the operation lid 16A. When the operation lid 16A is opened, the operation panel 16 (FIG. 2) for carrying out various kinds of operations of the air filtering apparatus 1 is exposed to the outside, and when the tank opening/closing lid 14A is opened, a water supply tank 41 (FIG. 2) described later is allowed to be taken in and out through a tank taken-out port 14. The operation panel 16 is formed to be elongated in parallel to the air blow-out port 13.

Furthermore, grip portions 17 are formed at the upper portions of both the side surfaces of the housing 11. These grip portions 17 are recess portions to which hands are hooked when the housing 11 is carried by the hands, and the air filtering apparatus 1 can be lifted and moved by one person when carried.

An upper front panel 18 (face panel) and a lower front panel 19 are freely detachably arranged in the vertical direction at the front side (front surface and one side surface) of the housing 11, and the internal construction of the housing 11 is exposed when the upper front panel 18 and the lower front panel 19 are detached. The lower front panel 19 has an arcuate portion 19A which is bent to the back side of the housing 11 is provided at the lower end portion of the lower front panel 19, and the air suction port 15 is formed at the arcuate portion 19A.

Next, the internal construction of the air filtering apparatus 1 will be described.

Figure 2:
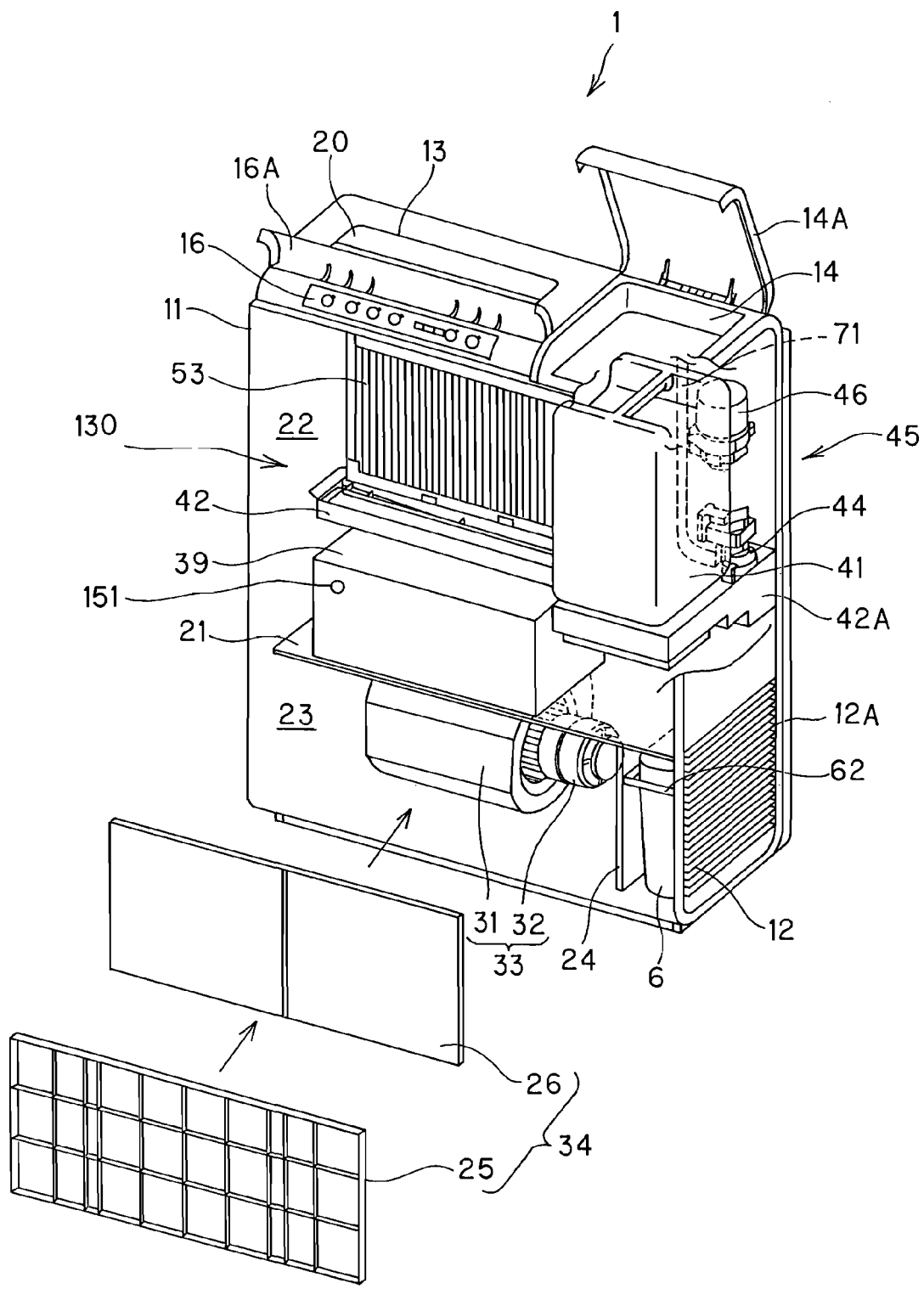
FIG. 2 is a perspective view showing the internal construction of the air filtering apparatus.

As shown in FIG. 2, a support plate (partition plate) 21 for partitioning the inside of the housing 11 into upper and lower chambers 22 and 23 is provided to the housing 11. In the lower chamber 23, an air blower 33 having an air blowing fan 31 and a fan motor 32 is disposed at the left side of the housing 11 in front view, and a drain tank 6 having a handle (grip portion) 62 is provided at the right side of the housing 11 so that the drain tank 6 can be pulled out to the front side of the housing 11. The air blower 33 and the drain tank 6 are separated from each other through a partition plate 24. The air blower 33 (the air blowing fan 31 and the fan motor 32) and the drain tank 6 are arranged in juxtaposition with each other.

Furthermore, a pre-filter 34 is freely detachably disposed so as to face the lower front panel 19 (FIG. 1) in the lower chamber 23. The pre-filter 34 comprises a first filter 25 for collecting large-size particles such as dust, etc. in the air sucked through the air suction port 12 and the air suction port 15, and a second filter 26 for collecting materials which pass through the first filter 25 and have particle sizes of 10 (μm) or more. Pollen, dust, etc. floated in the air can be removed by the pre-filter 34, and the air from which these materials are removed is supplied to the upper chamber 22 through the air flowing fan 31.

On the other hand, in the upper chamber 22, the electrical component box 39 is disposed above the air blower 33 (the air blowing fan 31 and the fan motor 32), and the gas-liquid contact member 53 is disposed above the electrical component box 39 so as to be erected. A water receiving tray 42 for receiving water dropped from the gas-liquid contact member 53 is disposed between the gas-liquid contact member 53 and the electrical component box 39. This water receiving tray 42 is equipped with a stock portion 42A having a deep bottom, and the stock portion 42A extends to the upper side of the drain tank 6. Various kinds of electrical components such as a control board having various kinds of devices constituting a controller for controlling the air filtering apparatus 1, a power supply circuit for supplying a power source voltage to the fan motor 32, etc. are accommodated in the electrical component box 39. A water supply tank 41 for stocking tap water or the like used for generate electrolytic water is disposed above the stock portion 42A so that water can be supplied from the water supply tank 41 to the stock portion 42A. In details, a float valve is provided to a water supply port formed at the lower end of the water supply tank 41, and the float valve is opened when the water level of the stock portion 42A is lower than the water supply port, whereby a required amount of water is supplied from the water supply tank 41 and the water level of the stock portion 42A is kept constant.

Figure 3:
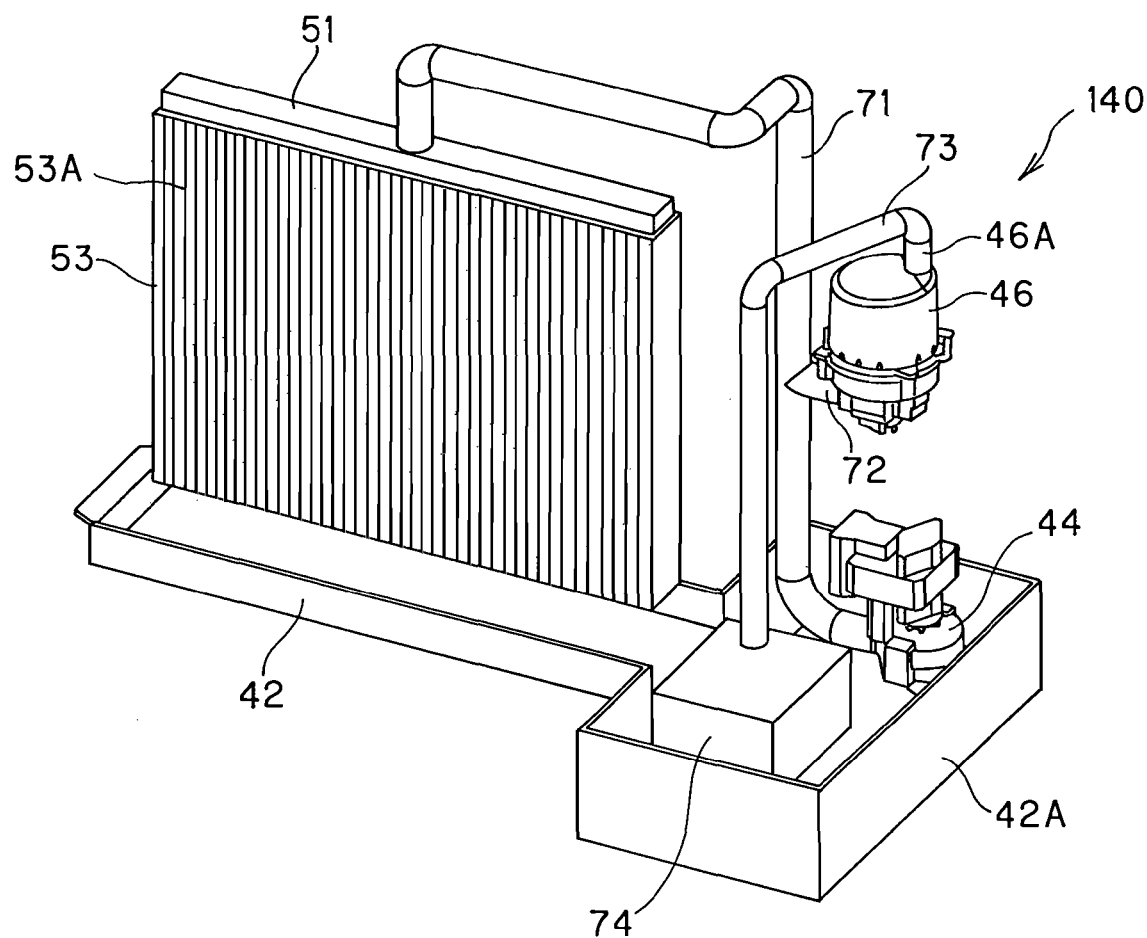
FIG. 3 is a perspective view showing a gas-liquid contact member and an electrolytic water generating unit.

As shown in FIGS. 2 and 3, an electrolytic water generating unit 45 for generating electrolytic water to be supplied to the gas-liquid contact member 53 is disposed above the stock portion 42A. The electrolytic water generating unit 45 comprises a circulating pump 44 and an electrolytic bath 46, and the circulating pump 44 is operated to change the rotational number thereof according to the control of the controller, whereby the circulation amount can be changed. A supply pipe 71 for having water stocked in the stock portion 42A and supplying the water to the gas-liquid contact member 53, and the electrolytic bath 46 is connected to the supply pipe 71 through a branch pipe 72 branched between the circulating pump 44 and the gas-liquid contact member 53. The electrolytic bath 46 contains plural electrodes as described above, and a voltage supplied from the controller is applied between these electrodes, whereby water is electrolyzed and electrolytic water is generated. A discharge port 46A for discharging the electrolytic water generated in the electrolytic bath 46 is formed on the top surface of the electrolytic bath 46, and a return pipe 73 for feeding back the electrolytic water to the stock portion 42A is connected to the discharge port 46A.

Furthermore, a filter member 74 for collecting solid materials contaminated in water flowing into the stock portion 42A is disposed above the stock portion 42A. The filter member 74 removes the solid materials (insoluble matters) contained in water falling from the gas-liquid contact member 53. In this construction, the return pipe 73 is disposed above the filter member 74, and water discharged from this return pipe 73 flows through the filter member 74 into the stock portion 42A of the water receiving tray 42. Solid materials (for example, scale discharged from the electrolytic bath 46, etc.) contained in water circulated through the water receiving tray 42 to the gas-liquid contact member 53 and the electrolytic water generating unit 45 are collected by this filter member 74. Therefore, these solid materials can be prevented from flowing into the gas-liquid contact member 53 and causing clogging of the gas-liquid contact member 53.

Furthermore, the filter member 74 is disposed in the stock portion 42A of the water receiving tray 42 while the upper portion thereof is opened, and thus the exchange timing of the filter member 74 can be simply judged by visual observation. Furthermore, when the filter member 74 is exchanged, the filter member 74 disposed at the entrance portion of the stock portion 42A may be detached by fingers and exchanged by a new one. Therefore, no tool is required and the maintenance can be simply performed. In this embodiment, the electrolytic water circulating unit 2 is constructed by the water receiving tray 42, the electrolytic water generating unit 45 (the circulating pump 44 and the electrolysis bath 46) and the gas-liquid contact member 53, and electrolytic water is circulated among these units.

Still furthermore, water stocked in the water receiving tray 42 is allowed to be properly discharged. Specifically, a drain pipe 55 (FIG. 8A) is joined to the lower portion of the stock portion 42A, and also a drain valve 56 (FIG. 8A) for opening/closing the drain pipe 55 is also provided. The tip of the drain pipe 55 extends to the upper side of the drain tank 6, and water in the water receiving tray 42 is discharged to the drain tank 6.

The gas-liquid contact member 53 is a member for bringing electrolytic water into contact with air supplied to the gas-liquid contact face 53A through an air flow passage described later. In the gas-liquid contact member 53, air sucked into the housing 11 is brought into contact with electrolytic water containing predetermined active oxygen species, whereby virus, etc. contained in the air is inactivated and thus the air is filtered.

A water sprinkle (or spray) box 51 for uniformly sprinkling (spraying, dispersing or the like) onto the gas-liquid contact member 53 is assembled to the upper portion of the gas-liquid contact member 53. The water sprinkle box 51 has at ray member for temporarily stocking electrolytic water, and plural water sprinkle holes (not shown) are formed in the side surface of the tray member and electrolytic water is dropped from the water sprinkle holes to the gas-liquid contact member 53.

Furthermore, the gas-liquid contact member 53 is a filter member having a honeycomb structure. In details, the gas liquid contact member 53 has a structure that an element portion coming into contact with air is supported by a frame. The element portion is constructed by stacking wave-shaped corrugated members and plate-shaped planar members, and a large number of substantially triangular openings are formed among the corrugated members and the planar members. Accordingly, the gas contact area when air is passed through the element portion can be kept broad, electrolytic water can be dropped to the element portion and also clogging hardly occurs.

Furthermore, in order to efficiently disperse electrolytic water dropped from the water sprinkle body 51 to the element portion, a water distributing sheet (not shown) is disposed on the top surface of the gas-liquid contact member 53. This water distributing sheet is formed of textile material having water permeability (for example, woven fabric, non-woven cloth or the like), and one or plural distributing sheets are provided along the cross-section to the thickness direction of the gas-liquid contact member 53.

Here, the respective portions of the gas-liquid contact member 53 (containing the frame, the element portion and the water distribution sheet) are formed of polyolefin resin (polyethylene resin, polypropylene resin or the like), PET (polyethylene/terephthalate) resin, vinyl chloride resin, fluorinated resin (PTFE, PFA, ETFE or the like), ceramic material or the like. In this embodiment, PET resin is used.

The respective portions of the gas-liquid contact member 53 are subjected to a hydrophilic treatment to enhance the affinity to electrolytic water, whereby water retentivity (wettability) of the gas-liquid contact member 53 to electrolytic water is kept, and the contact between active oxygen species (active oxygen material) described later and indoor air can be maintained for a long time. Furthermore, electrolytic water having mildew-proof action is dropped to the gas-liquid contact member 53, and thus breeding of molds, etc. can be avoided without taking any countermeasure (coating of mildew-proof agent or the like) to the gas-liquid contact member 53.

Next, the air flow in the air filtering apparatus 1 will be described.

As described above, the air blowing fan 31 is provided in the lower chamber 23 of the housing 11. The air blow port 31A of the air blowing fan is provided to be placed face up at the back side of the housing 11. An opening is formed in the support plate 21 so as to be overlapped with the air blow port 31A. The opening of the support plate 21 intercommunicated with a space (back side space) 1A as an air path (air flow passage) extending vertically at the back side of the upper chamber 22. Therefore, air blown out from the air blow port 31A of the air blowing fan 31 passes through the space 1A as indicated by an arrow in FIG. 4 and blown to the back surface of the gas-liquid contact member 53.

Figure 4:
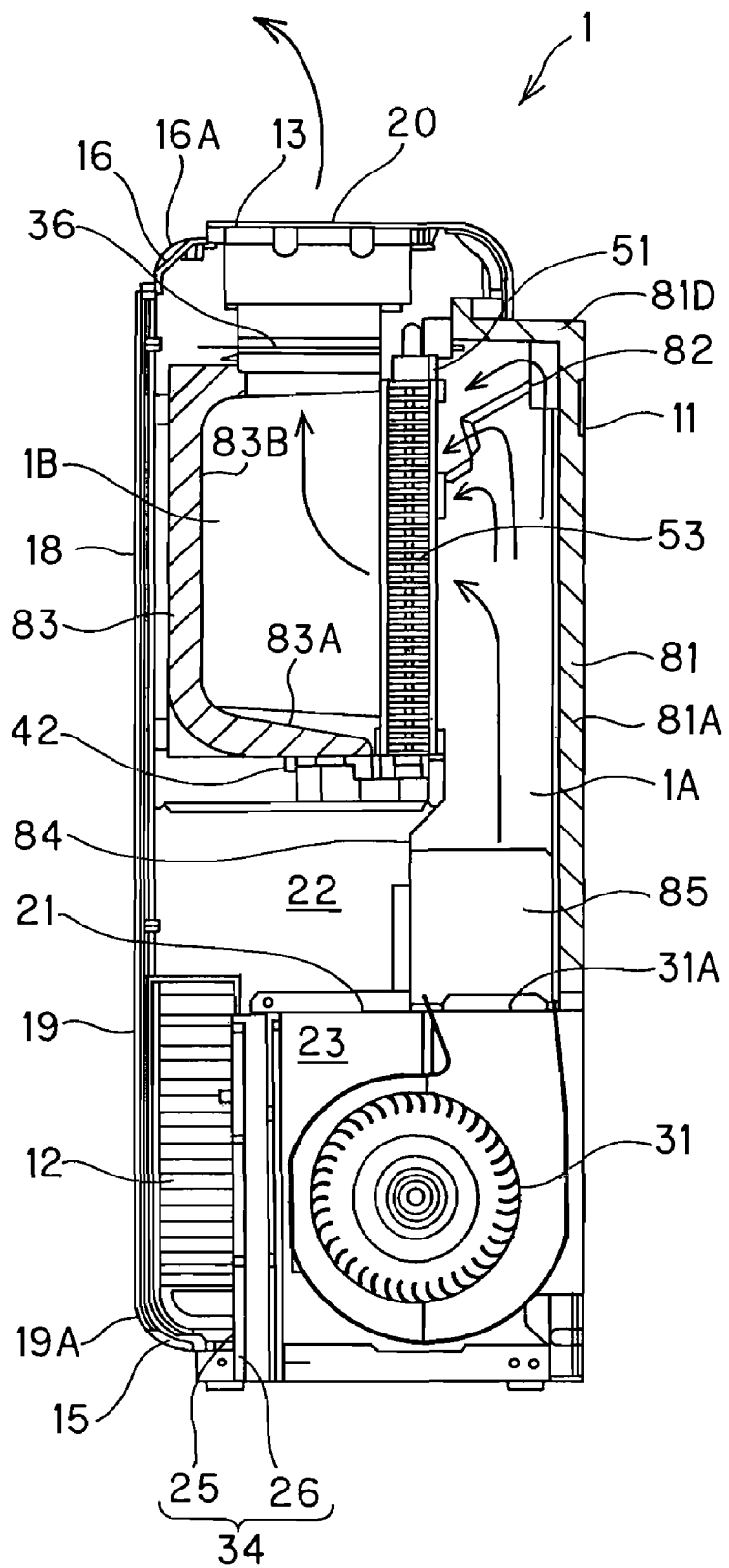
FIG. 4 is a right-side sectional view showing the internal construction of the air filtering apparatus.

In this construction, as shown in FIG. 4, the space 1A is defined by a first air guide member 81 disposed at the back side of the housing 11 and an air guide plate 84 extending from the support plate 21 to the water receiving tray 42. Furthermore, as shown in FIG. 5, a pair of air flow direction plates 85 are disposed below the space 1A, that is, at the edge portion of the opening of the support plate 21 to expand the air blown out from the opening (the air blow port 31A of the air blowing fan 31) in the width direction of the space 1A (in the X direction in FIG. 5).

Figure 6:
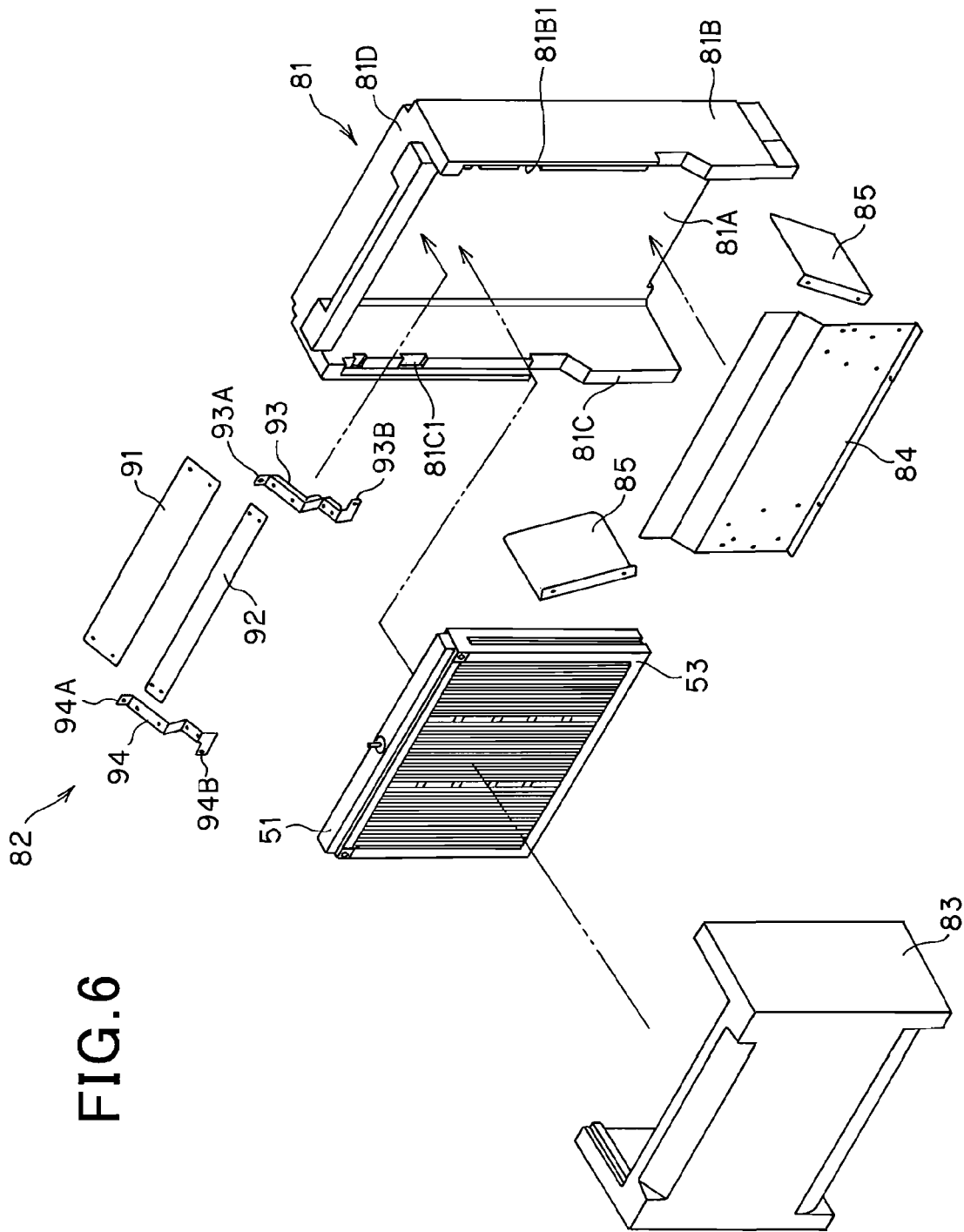
FIG. 6 is an exploded perspective view showing members defining spaces formed before and after the gas-liquid contact member.

As shown in FIG. 6, the first air guide member 81 has a back portion 81A, side portions 81B, 81C extending forwardly from both the end portions of the back portion 81A, and an upper portion 81D extending forwardly from the upper end portion of the back portion 81A. The upper portion 81D is joined to the upper end portions of the side portions 81B, 81C, and the first air guide member 81 is designed in a substantially box-shape while the front and lower surface portions thereof are opened. In this construction, the first air guide member 81 is formed of resin material such as styrol resin or the like.

When air blown out from the air blowing fan 31 is guided to the gas-liquid contact member 53 through the space 1A formed by the first air guide member 81, it is desired to uniformly blow air onto the whole surface of the gas-liquid contact member 53. However, the gas-liquid contact member 53 has such a tendency that air from the air blowing fan 31 is more easily passed through the gas-liquid contact member 53 at a position farther from the air blowing fan 31 (the upper portion of the gas-liquid contact member 53 in this construction) than that at a position nearer to the gas-liquid contact member 53 (the lower portion of the gas-liquid contact member 53), and thus has a problem that unevenness in air distribution in the height direction of the gas-liquid contact member 53 occurs and the air filtering performance of the gas-liquid contact member 53 cannot be sufficiently exercised. However, according to this embodiment, in order to solve this problem, an air distributing member (suppressing member 82 for suppressing the air flow amount at the upper portion of the gas-liquid contact member 53 is disposed above the space 1A as shown in FIG. 4. The air distributing member 82 increases the air flow resistance above the space 1A to suppress the air flow amount at the upper portion of the gas-liquid contact member 53, whereby the air blown out from the air blowing fan 31 is substantially uniformly blown to the gas-liquid contact member 53, so that's the air filtering capability of the gas-liquid contact member 53 can be sufficiently exercised.

Figure 5:
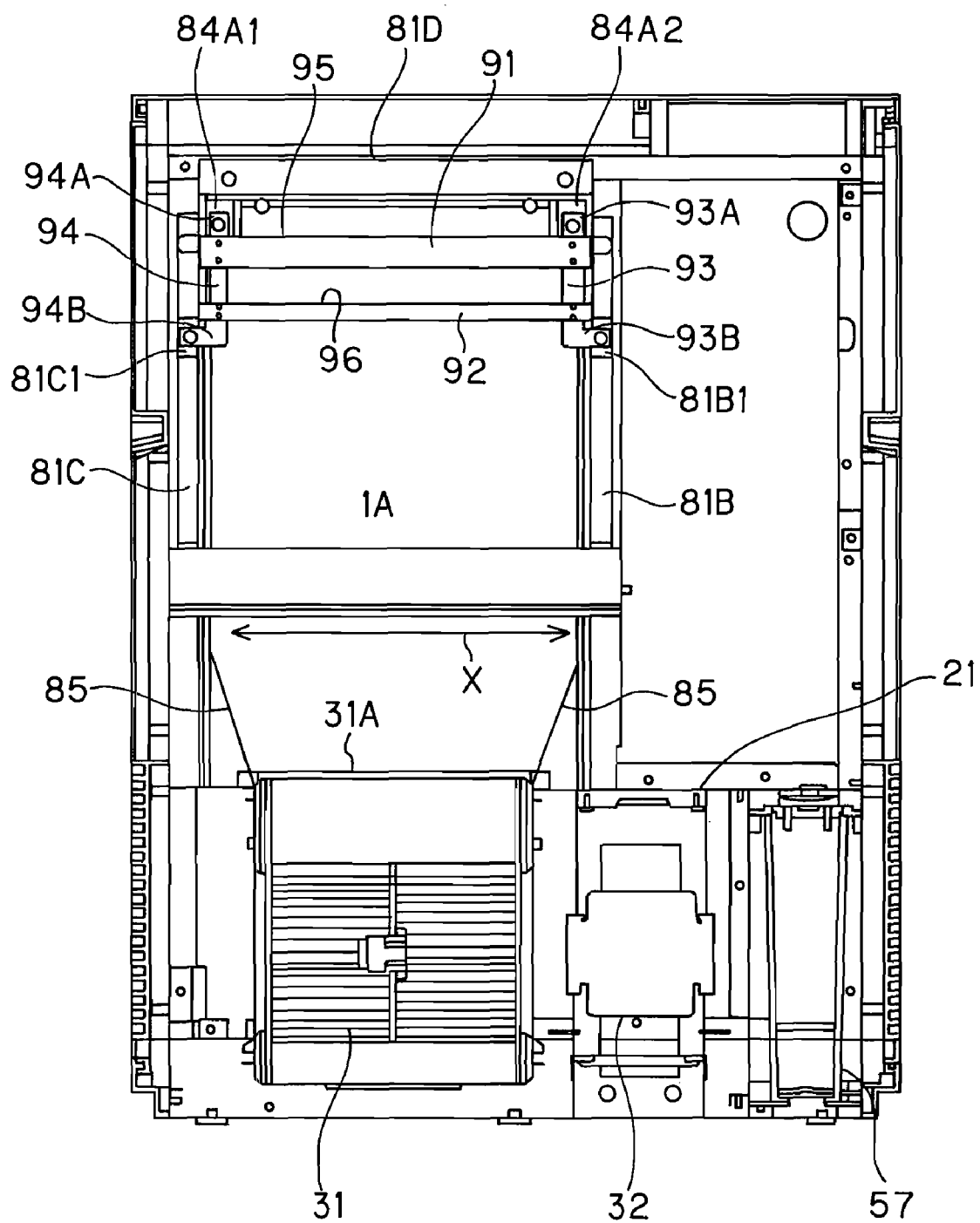
FIG. 5 is a front-side sectional view showing a space in which air flown from an air blowing fan flows.

As shown in FIG. 5, the air distributing member 82 comprises support members 93, 94 secured to the first air guide member 81 and two first and second air dividing plates 91 and 92 suspended between the support members 93 and 94. These first and second air dividing plates 91 and 92 are joined to the support members 93 and 94 by screw fixing or welding. The upper end portions 93A, 94A of the support members 93, 94 are fixed to fixing portions 84A1 and 84A2 formed at both the corner portions of the upper side of the back side portion 81A of the first air guide member 81 by screws. Furthermore, the lower end portions 93B and 94B of the support members 93 and 94 are fixed to fixing portions 81B1 and 81C1 formed at the front side of the side portions 81B and 81C of the first air guide member 81. These fixing portions 84A1, 84A2, 81B1 and 81C1 are formed by embedding steel plates having threaded holes on the surface of styrol resin.

In this construction, the air distributing member 82 having the two air dividing plates 91 and 92 is integrally formed by using the support members 93 and 94, and the air distributing member 82 is fixed from the front side of the first air guide member 81 by screws. Therefore, the air distributing member 82 can be easily fixed.

Figure 7:
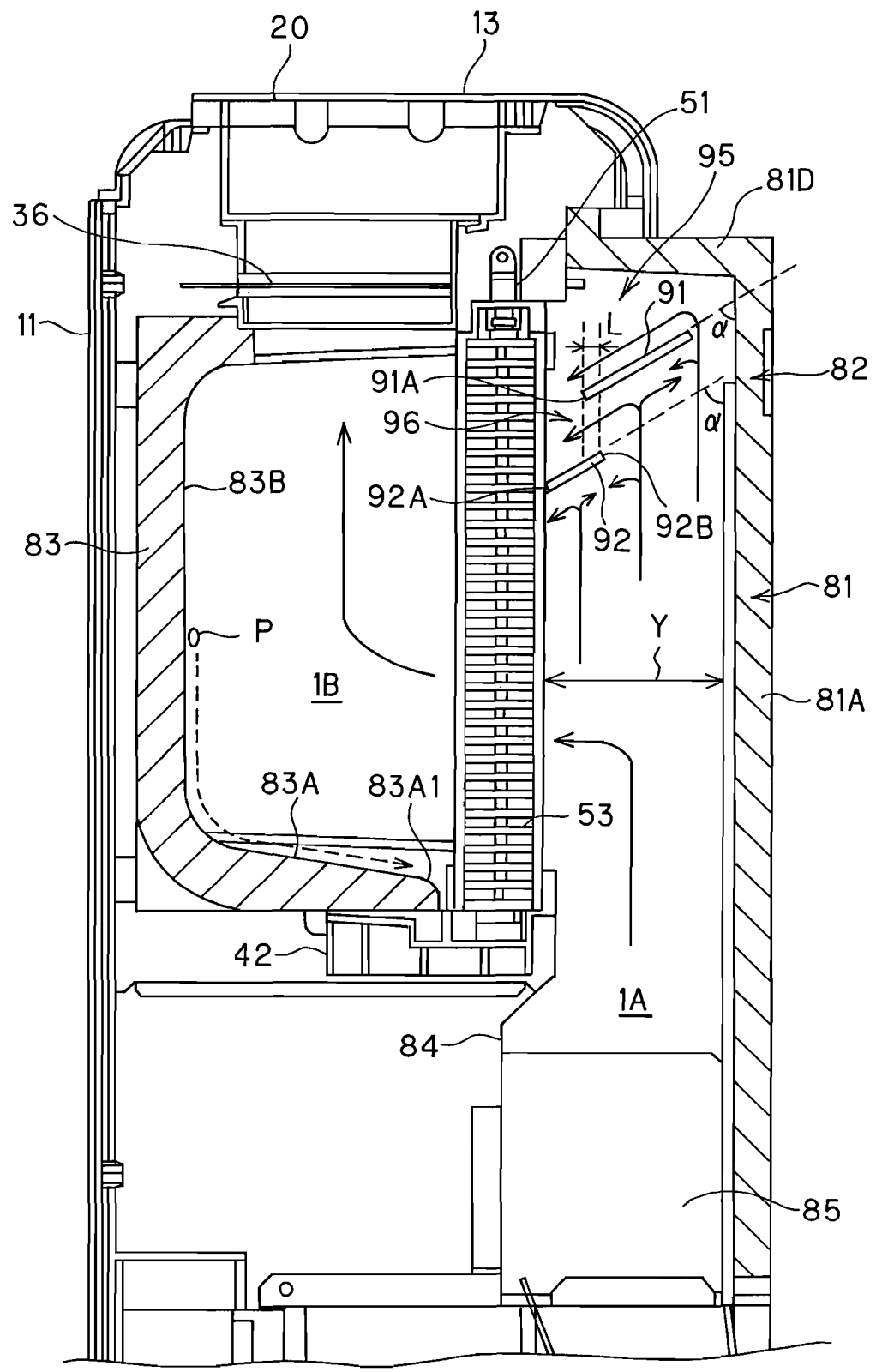
FIG. 7 is a partially enlarged view of FIG. 4.

Furthermore, as shown in FIG. 7, the first and second air dividing plates 91 and 92 are disposed so as to be positionally different from each other in height direction and downwardly inclined to the gas-liquid contact member 53. In FIG. 7, for convenience of description, the support members 93 and 94 are omitted from the illustration. The first air dividing plate 92 is disposed substantially at the same height as the upper end portion of the gas-liquid contact member 53, and the second air dividing plate 92 is disposed so as to be lower than the first air dividing plate 91, specifically, lower than the upper end portion of the gas-liquid contact member 53 by the distance corresponding to substantially a quarter of the height of the gas-liquid contact member 53. Accordingly, air guide paths 95 and 96 guided to the gas-liquid contact member 53 are formed between the first air dividing plate 91 and the upper surface portion 81D of the first air guide member 81 and between the first air dividing plate 91 and the second air dividing plate 92, respectively.

Furthermore, the first air dividing plate 91 and the second air dividing plate 92 are disposed so as to intersect to the back portion 81A of the first air guide member 81 at a predetermined angle α. If the angle α is increased (the angle α is set to approach to 90°), the air flow resistance can be increased, however, wind noise (noise caused by air flow) at the air dividing plates 91 and 92 is increased. Therefore, in this embodiment, the angle α is set to about 60° on the basis of experiments, etc.

As described, according to this embodiment, the air dividing plate 82 has the first air dividing plate 91 disposed so as to face the upper end portion of the gas-liquid contact member 53 and the second air dividing plate 92 disposed so as to be lower than the first air dividing plate 91, and the first and second air dividing plates 91 and 92 are disposed so as to be downwardly inclined to the gas-liquid contact member 53. Therefore, by the cooperation between the first and second air dividing plates 91 and 92, the air blown out from the air blowing fan 31 is distributed as indicated by an arrow of FIG. 7 and flows along each of the air guide paths 95 and 96, so that the air flow resistance at the upper portion of the gas-liquid contact member 53 is increased. Accordingly, the air flow amount at the upper portion of the gas-liquid contact member 53 is suppressed, so that the air flow amount at the lower portion of the gas-liquid contact member 53 is relatively increased.

Furthermore, the second air dividing plate 92 is disposed at the gas-liquid contact member 53 side so that the tip portion 92A thereof is substantially brought into contact with the gas-liquid contact member 53. The first air dividing plate 91 is disposed substantially at the center of the space 1A in the depth direction (in the Y direction in FIG. 7) so that the tip portion 91A of the first air dividing plate 91 is overlapped with the end portion 92B of the second air dividing plate 92 in top view. The first and second air dividing plates 91 and 92 are arranged so as to be overlapped with each other in top view as described above, whereby air can be prevented from being straightly upwardly blown between the first and second air dividing plates 91 and 92. Here, the length L of the overlapped portion between the first and second air dividing plates 91 and 92 is set to about 30 percentages of the width of the second air dividing plate 92 from experiments, etc.

Furthermore, a second air guide member (housing) 83 for guiding air passed through the gas-liquid contact member 53 is guided to the air blow-out port 13 is disposed in a space 1B at the opposite side to the space 1A with respect to the gas-liquid contact member 53 (at the front side of the housing 11 in this embodiment) as shown in FIG. 7. The second air guide member 83 is formed of resin material such as styrol resin or the like as in the case of the first air guide member, and it is designed in a substantially box-shape while the upper portion and the back portion are opened as shown in FIGS. 6 and 7.

The second air guide member 83 has a function of receiving water blown out to the space 1B (so-called scattered water) together with air from the gas-liquid contact member 53 in addition to the function of guiding air in the space 1B to the air blow-out port 13.

Specifically, the second air guide member 83 is formed so that the inner bottom surface 83A thereof is downwardly inclined to the gas-liquid contact member 53 and the tip portion 83A1 of the bottom surface 83A extends to the upper side of the water receiving tray 42 as shown in FIG. 7. Furthermore, this bottom surface 83A is smoothly connected to an inner surface 83B of the second air guide member 83 which faces the gas-liquid contact member 53. Therefore, water droplets P which are blown out from the gas-liquid contact member 53 to the space 1B together with the air impinge against the inner surface 83B of the second air guide member 83, and then flow along the inner surface 83B and the bottom surface 83A and return to the water receiving tray 42. Accordingly, water blown out from the gas-liquid contact member 53 together with blown-out air is not prevented from leaking to the outside, and thus it does not affect the electrical component box 39 (FIG. 2) located below the second air guide member 83, for example.

Furthermore, air passed through the gas-liquid contact member is guided to the surface 83B of the second air guide member 83, passed through an air blow-out port filter 36 disposed below the air blow-out port 13 and then discharged to the outside. The air blow-out port filter 36 prevents invasion of foreign materials from the air blow-out port 13 into the housing 11. The air blow-out port filter 36 has mesh, woven fabric, non-woven cloth or the like (not shown), and synthetic resin, preferably the material constituting the gas-liquid contact member 53 is used as the above materials. Furthermore, it is preferable that the air blow-out port filter 36 is burred to a moderate degree (i.e., has a properly loose texture) so that the air flow resistance of air passed through the gas-liquid contact member 53 is not remarkably increased.

Figure 8A:
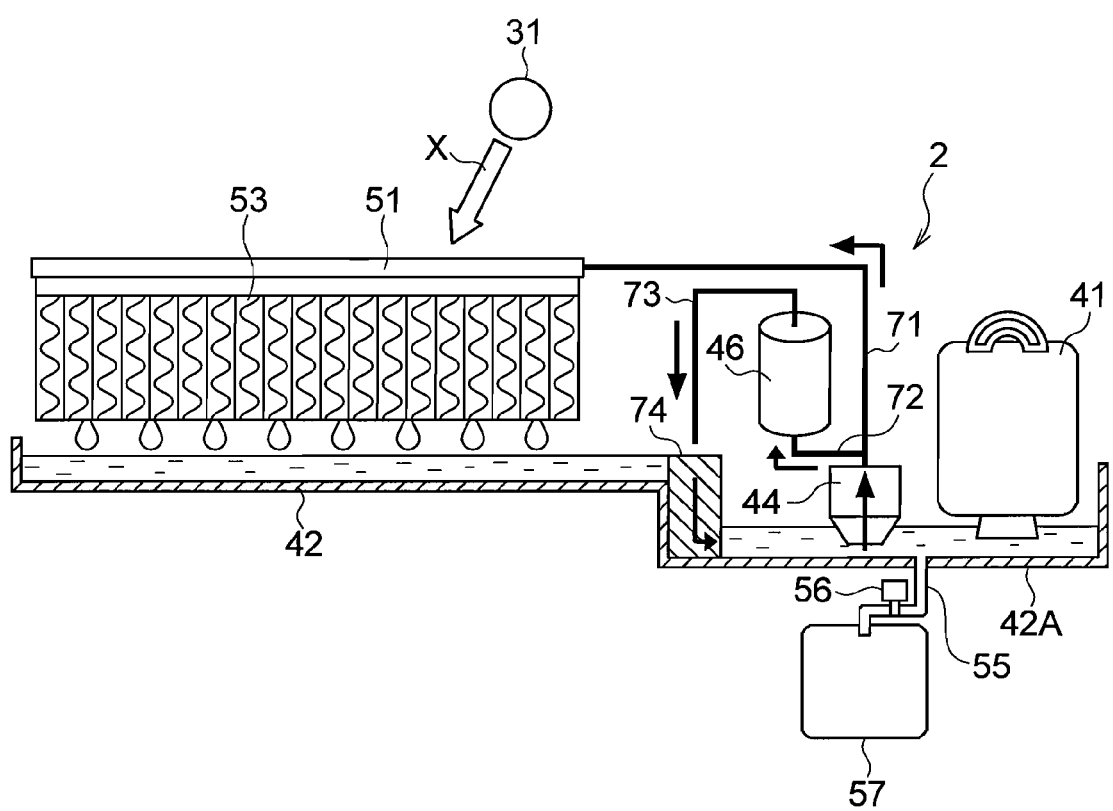
Figure 8B:
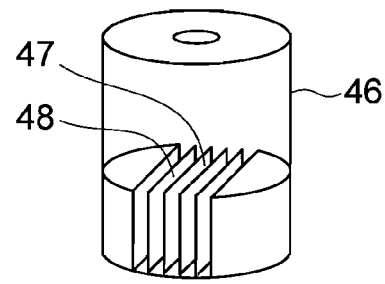

FIGS. 8A and 8B are diagrams showing an aspect of supply of electrolytic water. FIG. 8A is a diagram showing the construction of an air filtering mechanism and FIG. 8B is a detailed construction of the electrolytic bath 46. The supply of electrolytic water to the gas-liquid contact member 53 will be described with reference to FIG. 8. In this embodiment, the operation of the air filtering apparatus while tap water is filled in the water supply tank 41 will be described.

When the water supply tank 41 filled with tap water is set in the air filtering apparatus 1, tap water is supplied from the water supply tank 41 into the water receiving tray 42, and the water level of the water receiving tray 42 reaches a predetermined level. Water in the water receiving tray 42 is pumped up by the circulating pump 44 and a part thereof is supplied to the electrolytic bath 46. As shown in FIG. 8, the electrolytic bath 46 is equipped with at least a pair of electrodes 47 and 48, one electrode serving as an anode while the other electrode serves as a cathode. A voltage is applied between the electrodes 47 and 48 to electrolyze tap water flowing in the electrolytic bath 46, thereby generating electrolytic water containing active oxygen species.

Here, the active oxygen species is oxygen having higher oxidizing activity than normal oxygen and relevant materials thereto, and contain not only so-called narrowly-defined active oxygen such as superoxide anion, singlet oxygen, hydroxyl radical and hydrogen peroxide, but also so-called broadly-defined active oxygen such as ozone, hypochlorous acid, hypohalous acid, etc.

The electrodes 47, 48 are constructed by two electrode plates each of which comprises a base of Ti (titan) and a coated layer of Ir (iridium), Pt (platinum). The current value flowing in the electrodes 47, 48 is set so that the current density is equal to several mA (milliampere)/cm² (square centimeter) to several tens MA/cm², and a predetermined free residual chlorine concentration (for example, 1 mg (milligram)/l (liter) occurs.

More specifically, by supplying current to tap water through the electrodes 47, 48, the following reaction occurs at the cathode:

$$4H^+ + 4e^- + (4OH^-) \rightarrow 2H_2 + (4OH^-)$$

Furthermore, the following reaction occurs at the anode:

$$2H_2O \rightarrow 4H^+ + O_2 + 4e^-$$

At the same time, chlorine ions contained water (chlorine ions are added in tap water in advance) reacts as follows:

$$2Cl^- \rightarrow Cl_2 + 2e^-$$

Furthermore, Cl₂ thus generated reacts with water as follows:

$$Cl_2 + H_2O \rightarrow HClO + HCl$$

That is, hypochlorous acid (HClO) and hydrogen chloride (HCl) occur.

Figure 9:
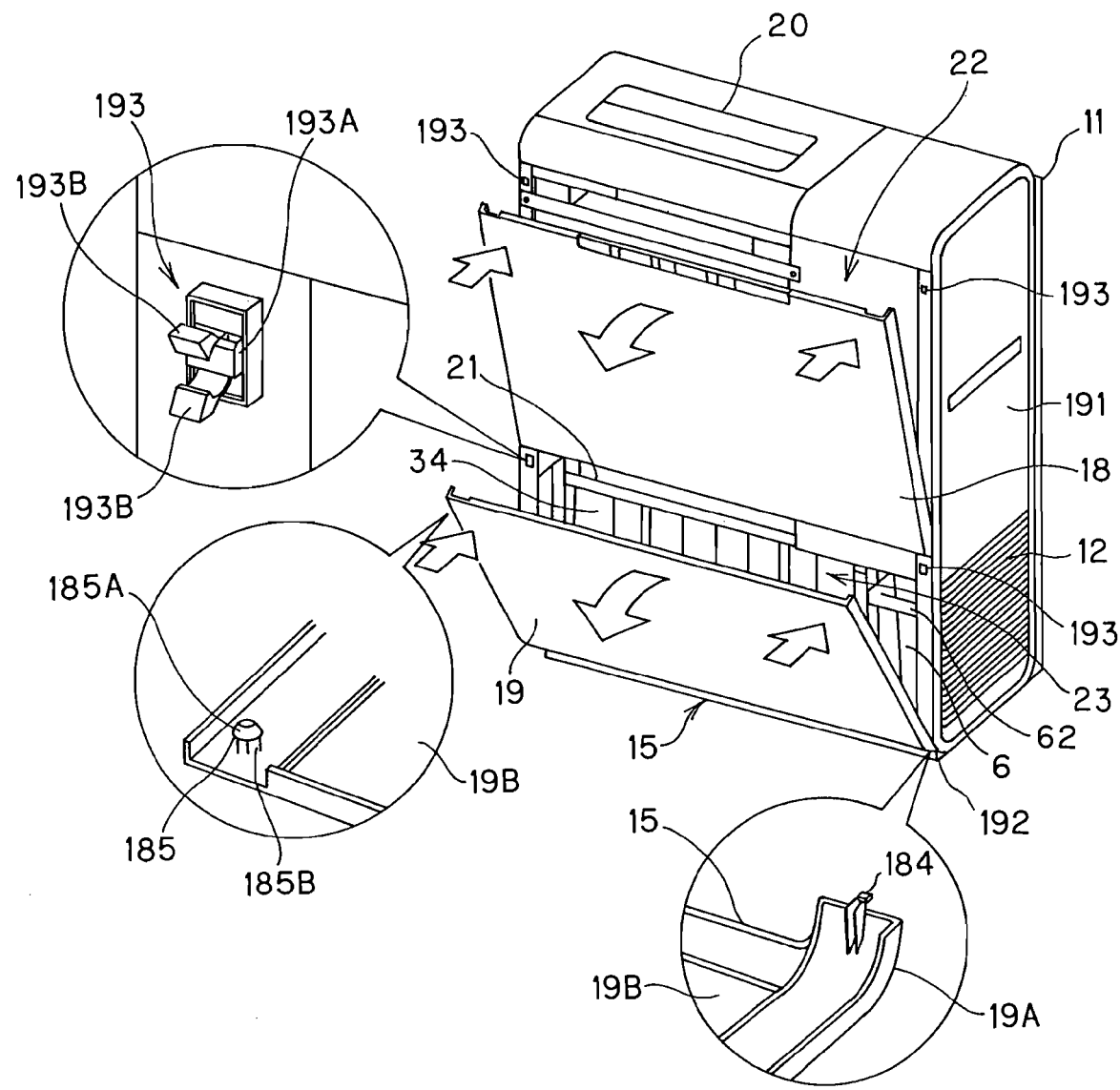
FIG. 9 is a diagram showing a mechanism for attaching/detaching an upper front panel and a lower front panel.

The concentration of the active oxygen species in the electrolytic water is adjusted so that virus, etc. to be filtered are inactivated. The adjustment of the concentration of the active oxygen species is performed by adjusting the voltage applied between the electrodes 47, 48 to adjust the value of current to flow between the electrodes 47, 48. Specifically, by changing the voltage applied between the electrodes 47, 48 to increase the current value, the concentration of hypochlorous acid in the electrolytic water can be increased.

Hypochlorous acid occurring at the anode is contained in the broadly-defined active oxygen species and has strong oxidizing action and a bleaching action. Water solution in which hypochlorous acid is dissolved, that is, electrolytic water generated in the air filtering apparatus 1 exercises various kinds of air cleaning effects such as inactivation of virus, etc., sterilization, decomposition of organic compounds, etc. When electrolytic water containing hypochlorous acid is dropped from the water sprinkle box 51 to the gas-liquid contact member 53, air blown out from the air blowing fan 31 is brought into contact with hypochlorous acid in the gas-liquid contact member 53. Accordingly, virus, etc. floating in the air are inactivated, and also odor materials contained in the air concerned react with hypochlorous acid to be decomposed or ionized, so that the order materials are dissolved in the water. Accordingly, air filtering and deodorization are performed, and cleaned air is discharged from the gas-liquid contact member 53. Furthermore, the electrolytic water containing hypochlorous acid is supplied to the gas-liquid contact member 53, whereby breeding of various bacteria, fungus, etc. in the gas-liquid contact member 53 can be prevented.

An inactivating mechanism of virus, etc. by the active oxygen species will be described by exemplifying influenza virus. The active oxygen species functions to break down and vanish (remove) the surface protein (spike) of the virus concerned which is indispensable for infection. When the surface protein of influenza virus is broken down, the influenza virus is not joined to a receptor which is necessary for infection of the virus concerned, so that infection can be prevented. Therefore, influenza virus floating in the air is brought into contact with the electrolytic water containing the active oxygen species in the gas-liquid contact member 53, so that the influenza virus loses so-called infection power, and thus the infection can be prevented.

Accordingly, even when the air filtering apparatus 1 is set in a so-called large space such as a kindergarten, an elementary/junior high/high school, long-term care insurance facilities, a hospital or the like, air cleaned (sterilized, inactivated, deodorized, etc.) by electrolytic water is enabled to broadly go around in a large space. Therefore, air filtering and deodorization in a large space can be efficiently performed.

Furthermore, the electrolytic water dropped from the water sprinkle box 51 to the gas-liquid contract member 53 moves downwardly along the gas-liquid contact member 53, and drops to the water receiving tray 42. The electrolytic water dropped to the water receiving tray 42 is pumped up by the circulating pump 44 again, and supplied through the electrolytic bath 46 to the gas-liquid contact member 53. As described above, a water circulation system is used in the construction of this embodiment, and air filtering can be efficiently performed over a long term by effectively using a small amount of water. Furthermore, when the amount of water circulated in the electrolytic water circulating unit 2 is reduced due to vaporization or the like, a proper amount of water in the water supply tank 41 is supplied to the water receiving tray 42.

In the air filtering apparatus 1 according to this embodiment, the upper front panel 18 and the lower front panel 19 are freely detachably mounted to the front surface of the housing 11 as described above. As shown in FIG. 9, the lower front panel 19 has lower hooks 184 formed at the lower end portions (arcuate portions 19A) of the lower front panel 19 and upper hooks 185 formed at the upper end portions of the lower front panel 10.

The lower hook 184 are pawl members extending substantially in parallel to the panel face 19B of the lower front panel 19, and hooked and fitted to hook groove portions 192 formed at the front-side lower portions of both the side plates 191 of the housing 11. The upper hooks 185 are projections extending substantially vertically to the panel face 19B of the lower front panel 19, and the tip portions 185 thereof are formed to be larger in diameter than the base portions 185B thereof.

When the lower front panel 19 is secured to the housing 11, latch portions 193 to which the upper hooks 185 are fitted are formed at the positions corresponding to the upper hooks 185 at the front sides of both the side plates 191 of the housing 11.

The latch portion 193 has a base portion 193A movable in the depth direction of the housing 11, and pawl portions 193B which are joined to the upper and lower portions of the base portion 193A through hinges. These pawl portions 193B are opened/closed in accordance with the position of the base portion 193A. When the tip portion 185A of the upper hook 185 abuts against the surface of the base portion 193A and thus the base portion 193A is pressed in the depth direction of the housing 11, the pawl portions 193B are closed (i.e., approach to each other) in connection with the movement of the base portion 193A. When the base portion 193A is once pressed in the depth direction, it is held at the press-in position (not shown), and thus the tip portion 185A is pinched by the pawl portions 193B, so that the lower front panel 19 can be easily closed.

On the other hand, when the base portion 193A of the latch portion 193 is pressed in again through the upper hook 185, the holding of the base portion 193A is released, and the base portion 193A concerned is returned to the initial position (FIG. 9). In connection with this return, the pawl portions 193B are opened (i.e., they get away from each other), and thus the tip portion 185A of the upper hook 185 is separated from the pawl portion 193B, so that the lower front panel 19 can be easily opened. As described above, the lower front panel 19 can be easily attached to/detached from the housing 11 without using any tool.

With respect to the upper front panel 18, the same construction as the lower front panel 19 is provided, and thus the description is omitted.

When the lower front panel 19 is detached, the pre-filter 34 accommodated in the housing 11 and the drain tank 6 are exposed as shown in FIG. 9. The drain tank 6 is accommodated in the lower chamber 23 of the housing 11 so as to be adjacent to the pre-filter 34 and near to the side plate 191 side so that it can be taken in and out through the front surface of the housing 11 under the state that the lower front panel 19 is detached.

The depth of the drain tank 6 is set to be shorter than the depth of the chamber 23, and thus a space occurs at the front side of the drain tank 6 under the state that the drain tank 6 is accommodated in the housing 11. This space serves as an air flow passage through which air sucked from the suction grille 12 of the side plate 91 flows to the pre-filter 34.

By detaching the lower front panel 19, the drain tank 6 can be pulled out to the front side and water stocked in the drain tank 6 can be discarded as described later. Furthermore, by detaching the pre-filter 34 to the front side of the housing 11, dust adhering to the pre-filter 34 can be cleaned and removed.

Figure 10:
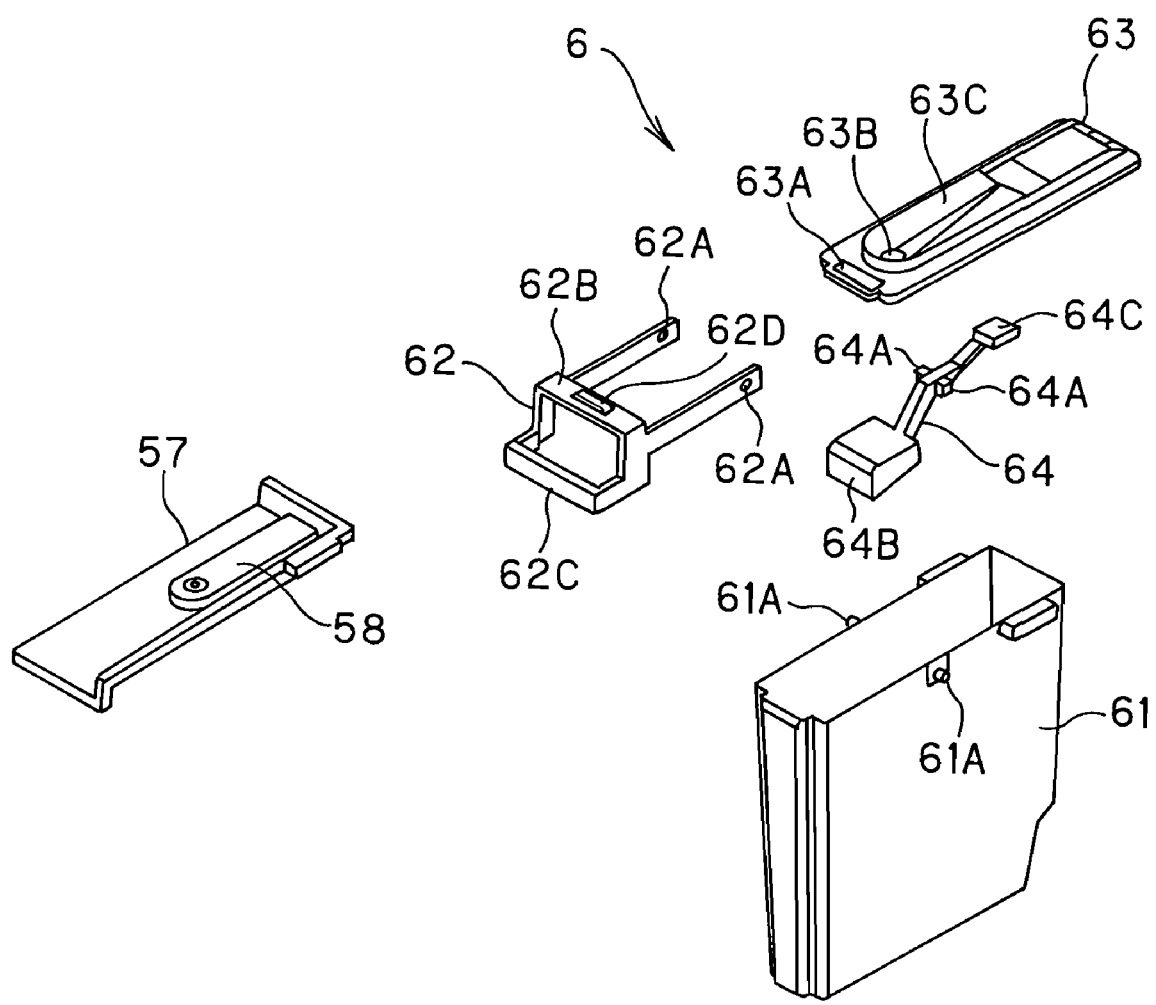
FIG. 10 is an exploded perspective view showing the construction of a drain tank.
Figure 11:
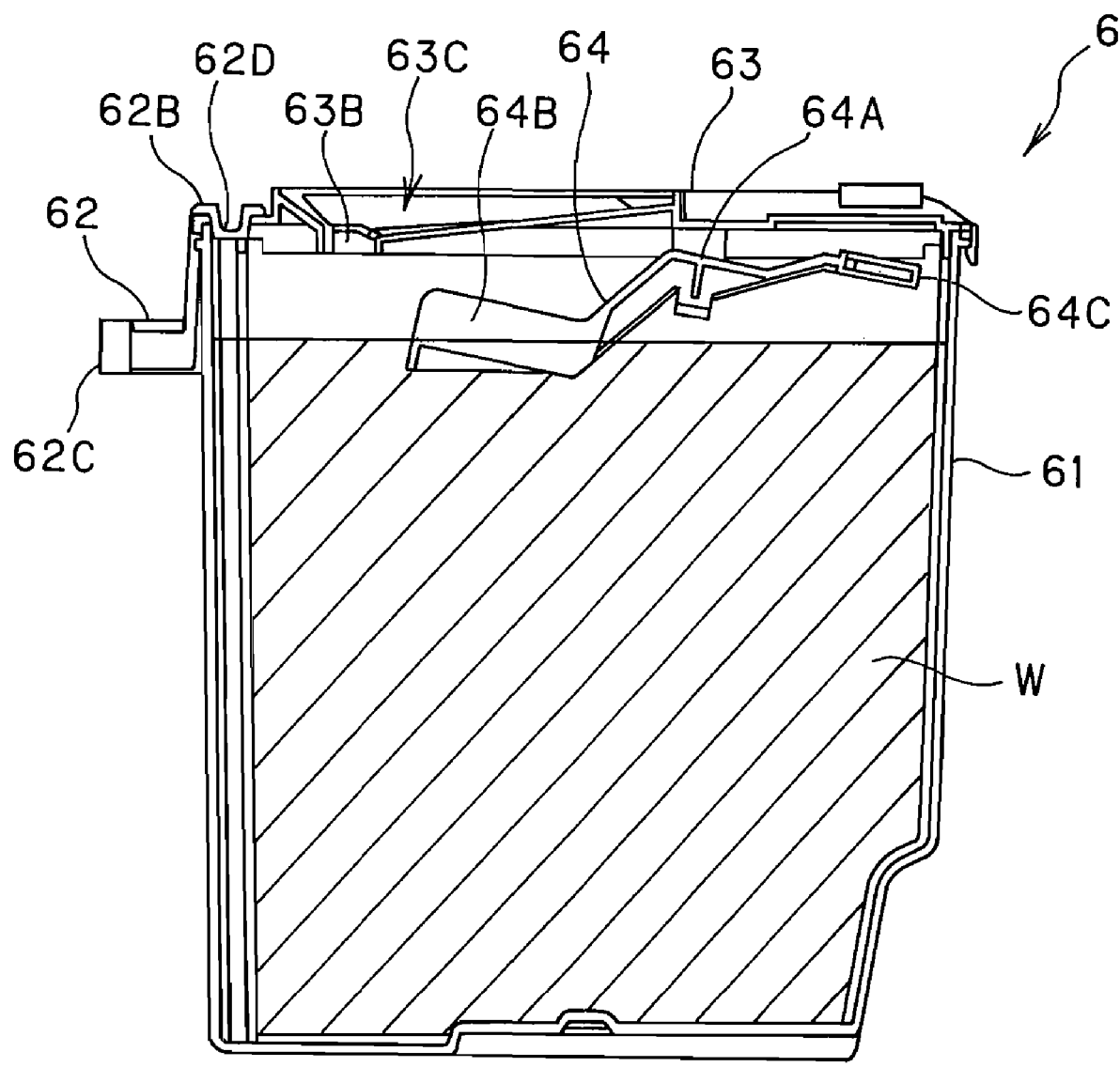
FIG. 11 is a cross-sectional view showing the construction of a drain tank.
Figure 12A:
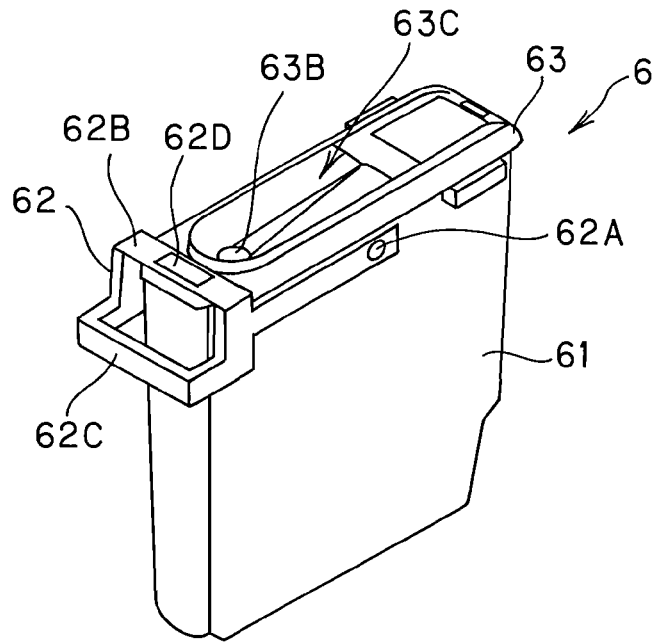
Figure 12B:
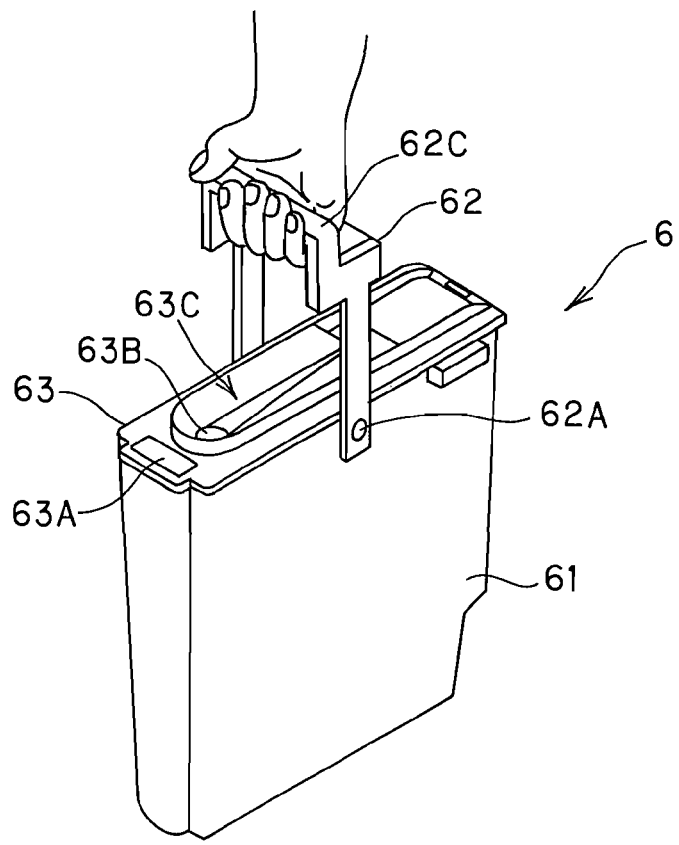
Figure 13:
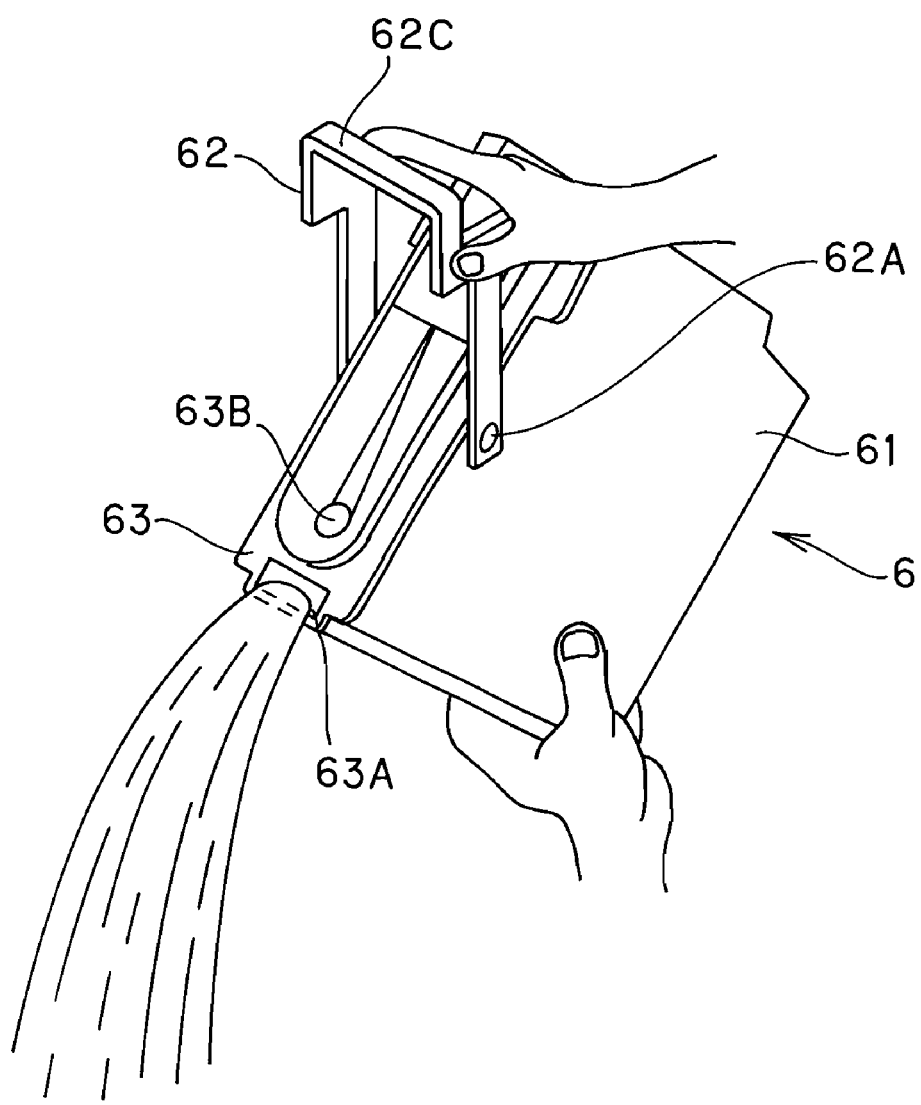
FIG. 13 is a diagram showing the operation of discarding water from the drain tank.

FIG. 10 is an exploded perspective view showing the construction of the drain tank 6, and FIG. 11 is a cross-sectional view showing the drain tank 6. A hatched portion represented by reference character W in FIG. 11 represents water. FIG. 12A is a perspective view showing the drain tank 6 taken out from the housing 11, and FIG. 12B is a perspective view showing the state that the drain tank is handled. FIG. 13 is a diagram showing the operation of discarding water from the drain tank 6. The drain tank 6 will be described hereunder with reference to these figures.

As shown in FIGS. 10 and 11, the drain tank 6 is constructed by a vertical tank body 61, a handle 62 serving as a grip when the drain tank is handled and a lid 63 covering the upper portion of the tank body 61, the handle 62 and the lid 63 being secured to the tank body 61. A float sensor 64 (displaceable member is disposed in the tank body 61.

The tank body 61 is a vertical container in which water drained from the electrolytic water circulating unit 2 (FIG. 8A) through the drain pipe 55, and the top surface thereof is opened. The shape of the cross-section of the tank body 61 is rectangular, elliptical or polygonal. Furthermore, a recess portion is formed at the lower portion of the tank body 61 so as to be fitted to projecting portions such as the frame, etc. of the housing 11 disposed around the drain tank 6. It is desired that the drain tank 6 can stand by itself under the state that it is detached from the housing 11. Therefore, the bottom structure of the drain tank 6 may be designed so that at least a part of the bottom surface is set to a flat surface or projections (legs) projecting to the ground plane are provided.

As shown in FIG. 10, shafts 61A projecting outwardly are formed substantially at the center of the tank body 61 in the depth direction. The handle 62 is freely swingably (rotatably) secured to the shafts 61A.

The handle 62 has two support arms which are fitted to the two shafts 61A formed on both the side surfaces of the tank body 61, and a fitting hole 62A is formed in the tip portion of each support arm. The handle 62 is swingable around the fitting hole 62A. The handle 62 has a flat-plate type base portion 62B and a rod-shaped grip portion 62C extending from the base portion 62B. The base portion 62B is a plate-shaped member for connecting the two support arms fitted to the shafts 61A, and it is equipped with a closing portion 62D for closing the drain port 63A described later. Furthermore, the grip portion 62C is formed at the tip side of the base portion 62B so as to extend substantially in parallel to the base portion 62B. The grip portion 62C may be a rod-shaped or plate-shaped member serving as a grip portion when the drain tank 6 is handled by a user.

Furthermore, as shown in FIGS. 7 and 8, the lid 63 is designed to have such shape and size that it is fitted to the opening portion of the top surface of the tank body 61 and covers the opening portion. A drain port 63A for discarding water in the tank body 61 is formed at one end portion of the lid 63. Furthermore, the lid 63 is provided with a drain receiving port 63B and a drain receiver 63C for pouring water passed and discharged from the electrolytic water circulating unit 2 (FIG. 5) through the drain pipe 55 into the tank body 61. The drain receiver 63C is formed on a downwardly inclined surface extending from the side edge portion of the lid 63 to the drain receiving port 63 to guide water dropped from the drain pipe 55 to the drain receiving port 63B. Under the state that the drain tank 6 is accommodated in the chamber 23, the opening portion of the lower end of the drain pipe 55 is located above the drain receiver 63C, and the water discharged from the drain pipe 55 drops from the drain receiving port 63B into the tank body 61 without leakage.

The drain port 63A provided to the lid 63 is a hole for discharging water stocked in the tank body 61 to the outside. The drain port 63A is normally closed by the closing portion 62D projecting to the back side of the base portion 62B, and the drain port 63A is opened by moving the handle 62.

Furthermore, a float sensor 64 is secured to the lower surface of the lid 63. The float sensor 64 is constructed by providing support shaft portions 64A at the center of an elongated body and also providing a float portion 64B to one end of the body while a magnet portion 64C is provided to the other end of the body. The support shaft portions 64A of the float sensor 64 are secured to the back side of the lid 63, and the float sensor 64 is freely swingable (rotatable) around the support shaft portions 64A. The magnet portion 64C is constructed by coating or wrapping magnet with resin or the like. The float portion 64B is formed of resin or the like which has low specific gravity.

The float sensor 64 is swingable (rotatable) with the support shaft portions 64A as supporting points. Normally, that is, under the state that no force is applied from the external, the float portion 64B side drops. Here, when water is nearly fully filled in the tank body 61 as indicated by reference character W in FIG. 8, the float portion 64B floats in the water, and the float sensor 64 swings around the support shaft portions 64A, and the magnet portion 64C is separated from the lid 63. Furthermore, under the state that the amount of water in the tank body 61 is further smaller than that under the fully-filled water level, the float portion 64B is located at a sufficiently drop position, and the magnet portion 64C is brought into contact with the back surface of the lid 63.

This construction can be implemented by adjusting the weight and buoyancy of the float portion 64B, the weight of the magnet portion 64C and the position of the support shaft portion 64A as a supporting point. The buoyancy of the float portion 64B can be easily adjusted on the basis of the specific gravity and the volume of the float portion 64B.

In the chamber 23 of the housing 11, a water level sensor portion 57 having a detector 58 for detecting approach of the magnet portion 64C is disposed above a position where the drain tank 6 is accommodated. The water level sensor portion 57 is located closely above the lid 63 under the state that the drain tank 6 is accommodated in the chamber 23. The detector 58 contains a movable magnetic member (not shown) and a detection circuit (not shown) whose conduction state is varied in connection with the movement of the magnetic member, and is disposed in conformity with the position to which the magnet portion 64C approaches. The detection circuit is connected to a controller mounted on a control board in the electrical component box 39 (FIG. 2).

The controller detects the presence or absence of the approach of the magnet portion 64C, whereby it can be detected whether the water level in the tank body 61 is equal or near to the water level under the fully filled state.

Here, the controller functions as both the detector 58 and detecting means. For example, when it detects that the drain tank 6 is nearly fully filled with water, the controller executes an operation such as turn-on of a lamp or the like on the operation panel 16 (FIG. 2), whereby the user is guided to discard water in the drain tank 6. Furthermore, the controller may open the drain valve 56 every predetermined time so that water in the water receiving tray 42 is discharged to the drain tank 6. However, when it is detected that the drain tank 6 is nearly fully filled with eater, the controller may control the drain valve 56 not to be opened.

Here, the materials constituting the respective parts of the drain tank 6, that is, the tank body 61, the handle 62, the lid 63 and the float sensor 64 may be any materials. However, as in the case of the respective parts of the gas-liquid contact member 53, it is preferable to use materials having little deterioration to electrolytic water, such as polyolefin resin (polyethylene resin, polypropylene resin or the like), PET (polyethylene terephthalate) resin, vinyl chloride resin, styrol resin, fluorinated resin (PTFE, PFA, ETFE or the like), ceramic materials, etc. for the portions which are brought into contact with electrolytic water.

The handling of the drain tank 6 will be described below.

Under the erected state shown in FIG. 12A, the handle 62 is brought into contact with the lid 63, and the drain port 63A is closed by the closing portion 62D. Furthermore, the grip portion 62C is projected to the front side of the drain tank 6. Therefore, when the drain tank 6 is taken out while the lower front panel 19 is opened as shown in FIG. 9, the drain tank 6 may be pulled out to the front side while the handle 62 is grasped by a hand, so that the drain tank 6 can be easily taken out.

Furthermore, as shown in FIG. 12B, when the grip portion 62C is pulled up, the handle 62 is turned around the fitting holes 62A. Under this state, the drain tank 6 can be lifted up while the grip portion 62C is grasped by a hand.

When the water stocked in the drain tank 6 is discarded, the drain tank 6 may be tilted under the state that the grip portion 62C is pulled up as shown in FIG. 13. Here, the lid 63 is fixed in close contact with the upper end of the tank body 61, so that water does not leak from any other portion than the drain port 63A.

According to this embodiment, electrolytic water discharged through the drain pipe 55 branched from the electrolytic water circulating unit 2 is stocked in the drain tank 6. Furthermore, the drain tank 6 has the vertically longer tank body 61, so that the drain tank 6 can be easily taken out from the front side of the housing 11 and the water stocked in the tank body 61 can be easily discarded. The tank body 61 is designed as a vertical type (i.e., vertically elongated), the space in which the drain tank 6 is mounted in the housing 11 can b easily secured. For example, as in the case of the above embodiment, the drain tank 6 is mounted in an empty space adjacent to the fan motor 32 in the lower chamber 23 of the housing 11, and thus it can be easily taken out from the housing 11 by merely detaching the lower front panel 19. As described above, according to the air filtering apparatus 1 of this embodiment, the drain tank 6 is disposed at the position where it can be easily taken out from the front surface of the housing 11 without losing the degree of freedom of the design of the air filtering apparatus 1, so that the work associated with the drainage can be easily performed.

Furthermore, when electrolytic water is circulated in the electrolytic water circulating unit 2, the high air filtering effect of the electrolytic water can be maintained by properly discharging electrolytic water and replacing it with fresh electrolytic water, so that the air filtering apparatus that can maintain the high air filtering effect can be implemented without increasing the load of the user.

The drain tank 6 is equipped with the handle 62 which is secured to the tank body 61 so as to be swingable (rotatable), so that the handle 62 can be moved to the position at which it is located in front of the tank body 61 and also the position at which it is located above the tank body 61. Therefore, under the state that the drain tank 6 is accommodated in the housing 1, the drain tank 6 can be easily pulled out from the front side of the housing 11 while the grip portion 62C of the handle 62 is grasped if the handle 62 is projected to the front side of the tank body 61, and thus the drain tank 6 can be easily taken in and out. In addition, if the handle 62 is titled to the front side of the tank body 61, the mount height of the drain tank 6 in the chamber 23 can be suppressed. Furthermore, under the state that the drain tank 6 is taken out from the housing 11, by moving the handle 62 to the position where it is projected to the upper side of the drain tank 6, the drain tank 6 can be easily handled while the handle 62 is grasped by a hand, so that the handling of the drain tank 6 can be easily performed.

Furthermore, according to this embodiment, the lid 63 is secured to the tank body 61, and the drain port 63A for discharging the water of the tank body 61 is formed in the lid 63. Under the state that the handle 62 is titled to the front side of the tank body, the drain port 63A is closed by the closing member 62D formed on the handle 62. Accordingly, in such a state that no water is discharged, for example, in the state that the drain tank 6 is accommodated in the housing 11, flow-out of water from the drain tank 6 can be prevented by closing the drain port 64A, and also the handle 62 is swung (turned) as occasion demands, thereby discharging water in the tank body 61. Accordingly, unintentional flow-out of water from the drain tank 6 can be surely prevented without losing the easiness of the work associated with the drainage.

Still furthermore, according to this embodiment, the lid 63 is provided with the drain receiver 63C for receiving water dropped form the drain pipe 55 and guiding the water into the tank body 61. Therefore, water leakage and water scattering in the housing 11 can be prevented without adding members.

Still furthermore, according to this embodiment, the float sensor 64 is provided so as to be displaced in accordance with the water level in the tank body 61, and the water level sensor portion 57 for detecting the displacement of the float sensor 64 is disposed in the housing 11. Therefore, the water level in the tank body 61 is detected and over-flow of water from the drain tank can be surely prevented. This float sensor 64 includes the float portion 64B floating in water stocked in the tank body 61 and the magnet portion 64C containing a magnet which are supported by the support shaft portions 64A, and the approach of the magnet portion 64C is detected by the detector 58 equipped to the water level sensor portion 57. Accordingly, it can be surely detected by a simple construction having an extremely low trouble risk that the water level in the tank body 61 is equal to a predetermined level or more, for example, it rises up to a full-filling water level or near to the full-filling water level. Accordingly, when the water level in the tank body 61 is high, the drain valve 56 can be controlled not to be opened, so that over-flow of water can be surely prevented. If the user is guided to discharge water by turning on the lamp or the like on the operation panel 16, the user can use the air filtering apparatus 1 with paying no attention to the water level of the drain tank 6, and the load associated with the management can be greatly reduced.

Furthermore, according to this embodiment, the lower front panel 19 has the lower hooks 184 formed at the lower portion of the lower front panel 19 and the upper hooks 185 formed at the upper portion, and the housing 11 has the hook groove portions 192 to which the lower hooks 184 are hooked and the latch portions 193 which are fitted to the upper hooks 185 are provided on the front sides of the side plates 191 of the housing 11. By fitting the upper hooks 185 to the latch portions 193 under the lower hooks 184 are hooked to the hook groove portions 192, the lower front panel 19 is secured to the housing 11. Therefore, the lower front panel 19 can be easily attached to/detached from the housing 11 without using any tool. Therefore, the work of taking out the drain tank 6 from the housing 11 can be extremely easily performed.

Furthermore, according to this embodiment, the gas-liquid contact member 53 erected in the housing 11, the electrolytic water generating unit 45 for generating electrolytic water to be supplied to the gas-liquid contact member 53 and the air blowing fan 31 for blowing air to the gas-liquid contact member 53 are provided, the space 1A as the air path for guiding air blown out upwardly from the air blowing fan 31 is formed in the housing 11, and the air distributing member 82 for suppressing the air flow amount at the upper portion of the gas-liquid contact member 53 is disposed. Therefore, the air flow amount at the upper portion of the gas-liquid contact member 53 is suppressed by the air distributing member 82, whereby the air flow amount at the lower portion of the gas-liquid contact member 53 is relatively increased. As a result, the unevenness of the air flow amount at the gas-liquid contact member 53 can be suppressed. Accordingly, the air can be substantially uniformly blown to the gas-liquid contact member 53, so that the air filtering capability of the gas-liquid contact member 53 can be sufficiently exercised.

Furthermore, according to this embodiment, the air distributing member 82 is disposed in the space 1A so as to face the upper portion of the gas-liquid contact member 53. Therefore, the air flow amount at the upper portion of the gas-liquid contact member 53 is suppressed to relatively increase the air flow amount at the lower portion of the gas-liquid contact member 53, so that unevenness of the air flow amount in the gas-liquid contact member 53 can be suppressed. Accordingly, air can be substantially uniformly blown to the gas-liquid contact member 53, so that the air filtering performance of the gas-liquid contact member 53 can be sufficiently exercised.

Still furthermore, according to this embodiment, the air distributing member 82 has the first air dividing plate 91 disposed so as to face the upper end portion of the gas-liquid contact member 53, and the second air dividing plate 92 disposed to be lower than the first air dividing plate 91, and the first shunt plate 91 and the second shunt plate 92 are disposed to be tilted downwardly to the gas-liquid contact member 53.

Therefore, the first and second air dividing plates 91 and 92 are cooperated with each other, so that air blown out from the air blowing fan 31 is distributed to flow to each of the air guide plates 95 and 96, so that the air flow resistance at the upper portion of the gas-liquid contact member 53 can be increased. Accordingly, the air flow amount at the upper portion of the gas-liquid contact member 53 is suppressed, so that the air flow amount at the lower portion of the gas-liquid contact member 53 is relatively increased. Furthermore, according to this embodiment, the first and second air dividing plates are disposed so as to be overlapped with each other in top view, so that air can be prevented from being straightly blown through the gap between the first and second air dividing plates 91 and 92.

The air filtering apparatus 1 of this embodiment is not limited to the above embodiment, and various modifications may be made without departing from the subject matter of the present invention.

For example, ozone ($O_3$) or hydrogen peroxide ($H_2O_2$) may be generated as active oxygen species. In this case, when platinum tantalum electrodes are used as the electrodes, active oxygen species can be highly efficiently and stably generated from water in which ion species are rare.

At this time, at the anode, the following reaction occurs:

$$2H_2O \rightarrow 4H^+ + O_2 + 4e^-$$

Simultaneously with the above reaction, the following reactions occur, and ozone ($O_3$) is generated.

$$3H_2O \rightarrow O_3 + 6H^+ + 6e^-$$

$$2H_2O \rightarrow O_3 + 4H^+ + 4e^-$$

Furthermore, at the cathode, the following reactions occur:

$$4H^+ + 4e^- + (4OH^-) \rightarrow 2H_2 + (4OH^-)$$

$$O_2^- + e^- + 2H^+ \rightarrow H_2O_2$$

That is, $O_2^-$ generated through the electrode reaction and $H^+$ in solution are bonded to each other to generate hydrogen peroxide ($H_2O_2$).

Furthermore, in the above embodiment, tap water is supplied from the water supply tank 41. Tap water is added with chlorine compound for the purpose of sterilization, and thus it contains chloride ions. Hypochlorous acid and hydrochloric acid are generated through the reaction of chloride ions. This is not limited to the case where tap water is used. Active oxygen species containing halogen can be generated through the same reaction insofar as water contains halide ions by adding or mixing halide to water supplied to the electrolytic bath 46.

In the air filtering apparatus 1, the same reactions can be also induced when water in which ion species is rare (containing pure water, purified water, well water, some kind of tap water or the like) is used. That is, if halide (salt or the like) is added to water in which ion species is rare, the same reactions are induced, and active species can be obtained. Furthermore, the above embodiment uses a water supply system based on the water supply tank 41 which can be freely taken in and out. In place of this water supply tank 41, a water distributing and supplying system in which a tap water pipe is connected to lead city water directly may be used.

Next, another embodiment will be described.

In the air filtering apparatus described above, in the case of the same current (power) supply state between the electrodes (the supply power amount (current value, current supply time or the like)), the condition of generating electrolytic water is varied in accordance with the water quality of tap water or the like supplied for electrolysis. For example, the concentration of electrolytic material such as chloride ion or the like contained in tap water is different between an urban area and a mountain-ringed region or the like. Therefore, even when predetermined power is supplied between the electrodes for a predetermined current supply time with a current value which is preset on the basis of the water quality of standard tap water in advance at the shipping time, it may be impossible to generate electrolytic water containing active oxygen species having a predetermined concentration required for air filtering in case of some types of tap water (water quality). Therefore, when the air filtering apparatus is set, the power supply (current supply) state between the electrodes is required to be changed in accordance with the water quality of tap water in that district. On the other hand, after the air filtering apparatus is once set, the water quality of tap water is hardly varied, and thus it is rate to change the setting associated with the power supply state. Furthermore, once the setting associated with the power supply state is unintentionally changed, the concentration of active oxygen species contained in electrolytic water is varied, and thus it is impossible to obtain a desired air filtering effect.

Therefore, a mechanism for properly changing the power (current) supply state between the electrodes used to generate electrolytic water in accordance with the water quality in the air filtering apparatus for generating electrolytic water and filtering air will be described by exemplifying an air filtering apparatus 100 shown in FIG. 14.

The air filtering apparatus 100 according to this embodiment has substantially the same construction as the air filtering apparatus 1, and the same elements as the air filtering apparatus 1 are represented by the same reference numerals, and the description thereof is omitted.

Figure 14:
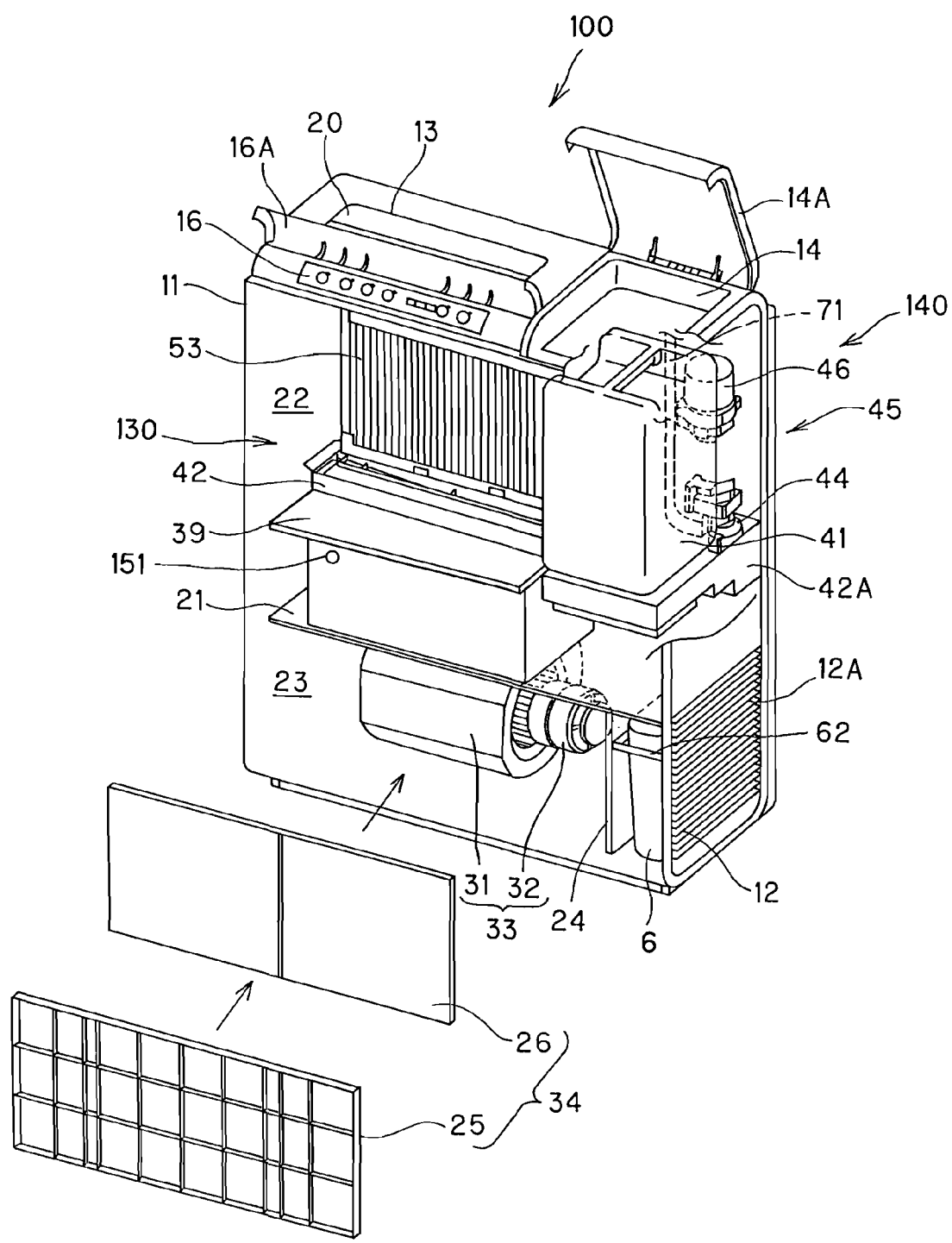
FIG. 14 is a perspective view showing an example of the internal construction of the air filtering apparatus according to another embodiment.

As shown in FIG. 14, the air filtering apparatus 100 has an air blower 33 for forming an air flow passage directing from air suction ports 12 and 15 formed in the housing 11 to the air blow-out port 13 in the housing 11, an air filtering unit 130 having a gas-liquid contact member 53 that is disposed on the air flow passage based on the air blower 33 and brings electrolytic water into contact with air supplied through the air flow passage, and a water supply tank 41, a circulating pump 44, an electrolytic bath (electrolytic water generating unit) 46 and a water receiving tray 42 as constituent elements of the electrolytic water circulating and supplying unit 140 for circulatingly supplying electrolytic water to the gas-liquid contact member 53.

As shown in FIG. 14, the gas-liquid contact member 53 is mounted at the left side above the partition plate 21 in front view and also an electrical component box 39 is mounted on the partition plate 21 at the left side. The water receiving tray 42 is mounted above the electrical component box 39, and the gas-liquid contact member 53 is disposed through the water receiving tray 42. Furthermore, the water supply tank 41 disposed below the operation lid 16A, the electrolytic bath 46 disposed at the rear side of the water supply tank 41 and the circulating pump 44 for supplying water in the water receiving tray 42 to the electrolytic bath 46 and the gas-liquid contact member 53 are disposed at the right side above the partition plate 21. These elements constitute the electrolytic water circulating and supplying unit 140.

The water supply tank 41 is a tank for stocking tap water or the like to be used to generate electrolytic water. The water supply port of the water supply tank 41 is disposed in the stock portion 42A of the water receiving tray 42, and a proper amount of water is supplied to the water receiving tray 42. However, water to be supplied to generate electrolytic water is not limited to tap water, and well water, pure water, purified water or the like may be used in place of tap water. However, as described later, electrolytic water is generated by electrolyzing water (containing electrolytic water generated in the electrolytic bath 46) in the electrolytic bath 46, and it is preferable that water containing predetermined ion species such as chloride ion or the like is stocked, for example. Therefore, when tap water containing a low concentration of ion species, well water, pure water, purified water or the like is used, it is preferable to add material containing predetermined ion species such as salt or the like as electrolysis promoting agent for promoting electrolysis.

Figure 15:
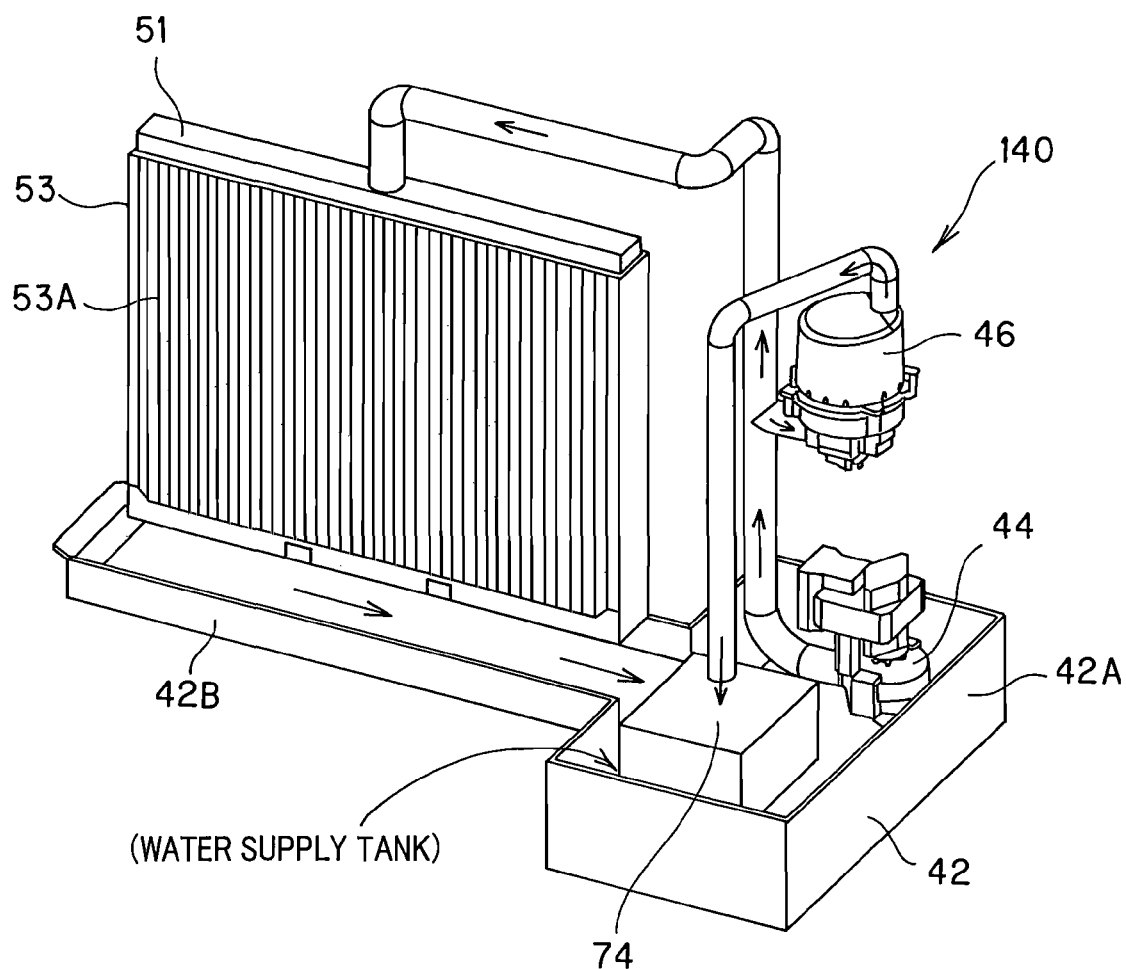
FIG. 15 is a diagram showing a circulating passage of electrolytic water in the air filtering apparatus.

Furthermore, as shown in FIG. 15, a water sprinkle (spray, dispersing or the like) box 51 as one of the constituent elements of the electrolysis circulating and supplying unit 140 is assembled to the upper portion of the gas-liquid contact member 53, and the water receiving tray 42 is disposed below the gas-liquid contact member 53. The water receiving tray 42 has the stock portion 42A in which the water suction port of the water supply tank 41 is disposed and a water receiving portion 42B which is disposed below the gas-liquid contact member 53 and receives electrolytic water discharged from the gas-liquid contact member 53. The circulating pump 44 is disposed in the stock portion 42A, and a filter member 74 for removing insoluble materials such as scale contained in electrolytic water generated in the electrolytic bath 46, etc. is disposed at the joint portion between the water receiving portion 42B and the stock portion 42A. The insoluble materials contained in electrolytic water discharged from the gas-liquid contact member 53 are removed. By disposing the filter member 74 as described above, water pumped up by the circulating pump 44 can be prevented from being contaminated with insoluble materials such as scale, pollen, etc.

In this embodiment, as shown in FIG. 15, the electrolytic water generated in the electrolytic bath 46 is supplied to the stock portion 42A through the filter member 74, and a part of the electrolytic water stocked in the stock portion 42A is supplied to the gas-liquid contact member 53 through the water sprinkle box 51 by the circulating pump 44 while the remaining electrolytic water is supplied to the electrolytic bath 46 again. As described above, the electrolysis is repetitively carried out by using electrolytic water in the electrolytic bath 46, whereby electrolytic water having a high concentration of active oxygen species can be generated. Furthermore, by circulating the electrolytic water discharged from the gas-liquid contact member 53, water may be supplemented from the water supply tank 41 by only the amount corresponding to an insufficient amount of water. Therefore a water resource can be effectively used.

When electrolytic water is generated, the concentration of the active oxygen species in the electrolytic water is adjusted so that virus, etc. to be filtered can be inactivated. The adjustment of the concentration of the active oxygen species is performed by adjusting the voltage applied between the electrodes 47 and 48 to adjust the current value flowing between the electrodes 47 and 48.

For example, when the current value flowing between the electrodes 47 and 48 is set to 20 mA/cm$^2$ in current density, in the case of hypochlorous acid, a predetermined free residual chlorine concentration (for example, 1 mg/liter) can be generated. The current value is adjusted by changing the voltage applied between the electrodes 47 and 48 so that the concentration of active oxygen species contained in electrolytic water can be adjusted, and basically the concentration of the active oxygen species in the electrolytic water can be increased by increasing the current value.

Figure 16A:
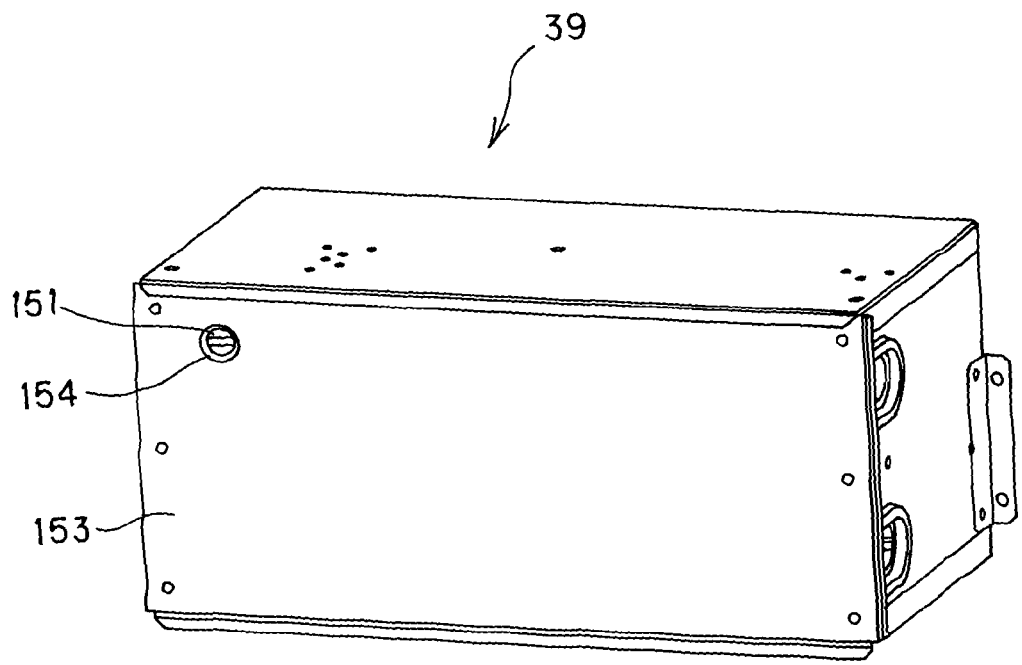
FIG. 16A is a perspective view showing an example of the outlook construction of the electrical component box provided in the housing of the air filtering apparatus.
Figure 16B:
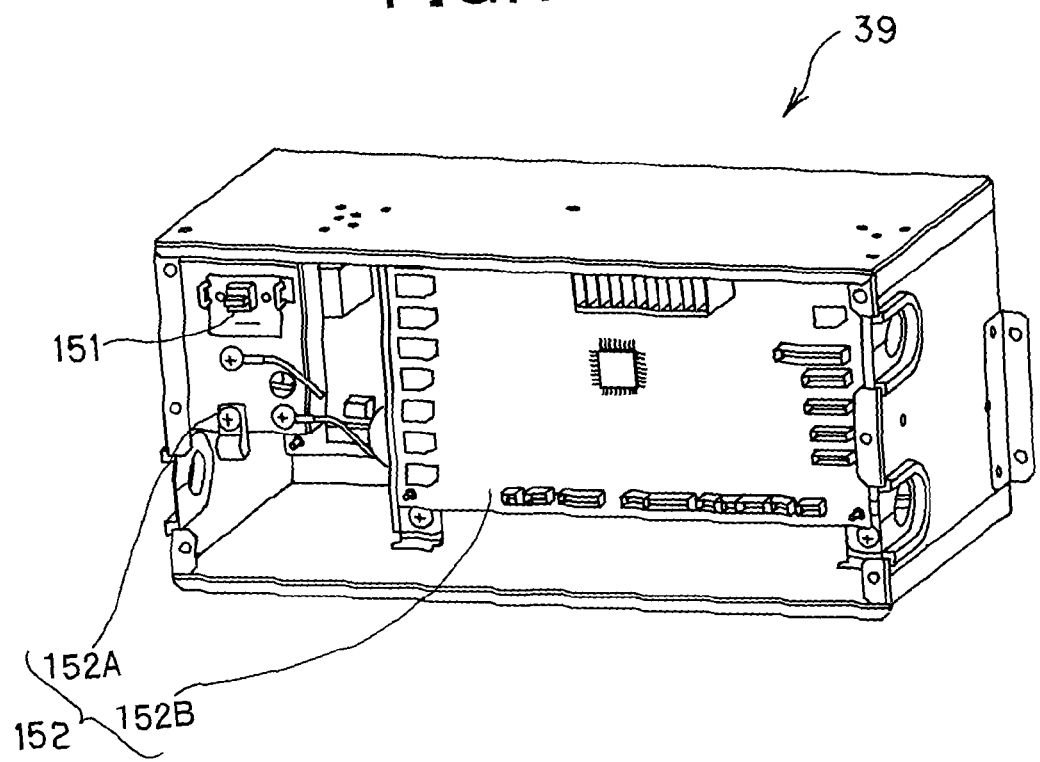
FIG. 16B is a perspective view showing an example of the internal construction.

In this embodiment, an rotary operation tab 151 (operating unit) for changing the power (current) supply state between the electrodes 47 and d48 of the electrolytic bath 46 when or after the air filtering apparatus 100 is set is provided to a controller 152 (control board 152A) accommodated in the electrical component box 39 as shown in FIGS. 16A and 16B (see FIG. 16B). The electrical component box 39 is used to accommodate various kinds of electrical parts as described above in addition to the control boards 152A and 152B in which CPU, RAM, ROM, etc. as the constituent elements of the controller 152 are disposed.

As shown in FIG. 16B, the rotary operation tab 151 is provided to the control board 152A so as to be located at the upper left side on the front surface of the electrical component box 39. Furthermore, as shown in FIG. 16A, the rotary operation tab 151 is disposed so as to be exposed to the outside through a hole 154 formed in the front panel 153 of the electrical component box 39.

Figure 17:
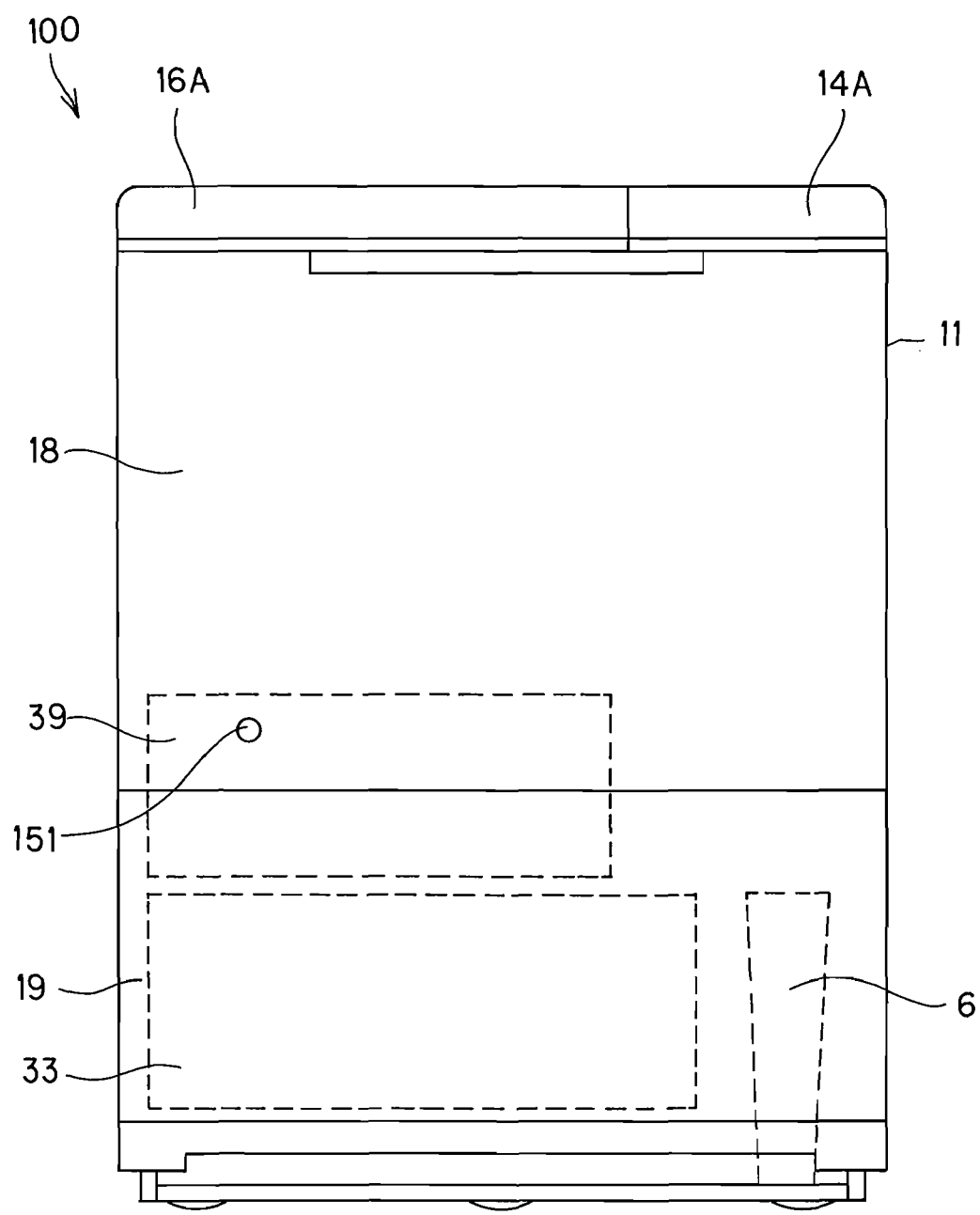
FIG. 17 is a front view showing an arrangement of the electrical component box in the housing by a broken line.

As shown in FIG. 14, the electrical component box 39 is disposed on the upper surface of the partition plate 21 so that the rotary operation tab 151 is exposed to the outside when the upper front panel (upper side front panel) 18 is detached from the housing 11 as shown in FIG. 17. Furthermore, as shown in FIG. 17, the boundary position between the upper front panel 18 and the lower front panel 19 is located substantially at the center position in the vertical direction of the electrical component box 39, and only the upper portion of the electrical component box 39 is exposed to the outside when the upper front panel 18 is detached from the housing 11. In FIG. 17, the electrical component box 39, the air blower 33 and the drain tank 6 are represented by broken lines.

Figure 18A:
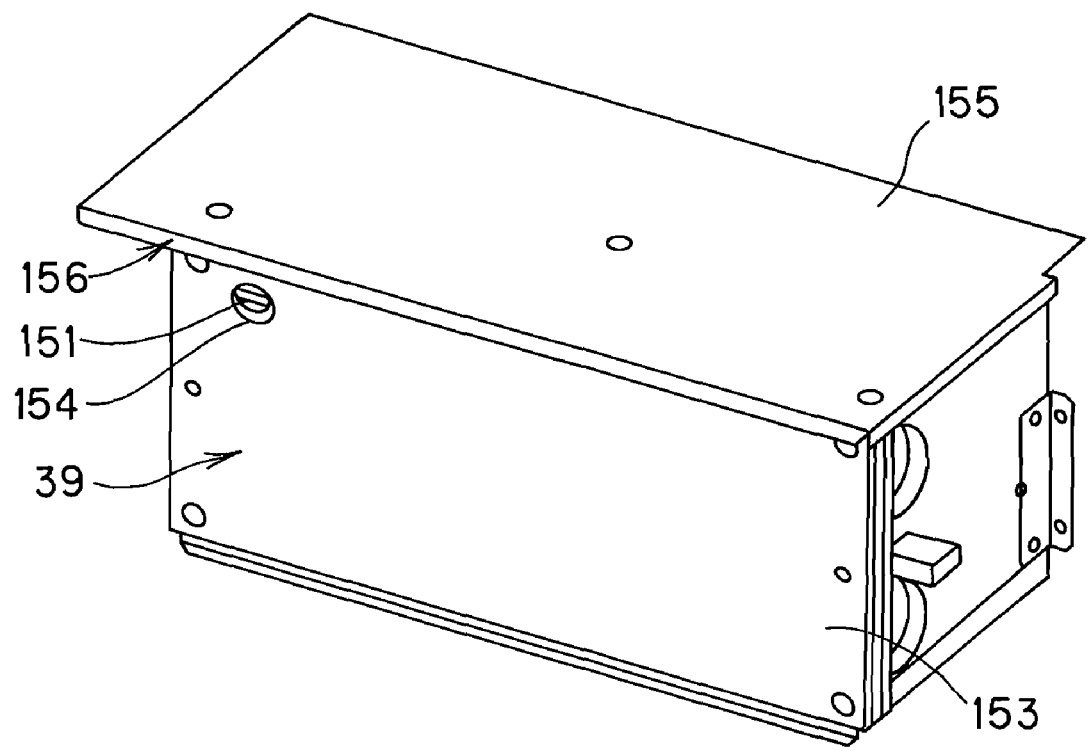
FIG. 18A is a perspective view showing a flange portion provided to the electrical component box.
Figure 18B:
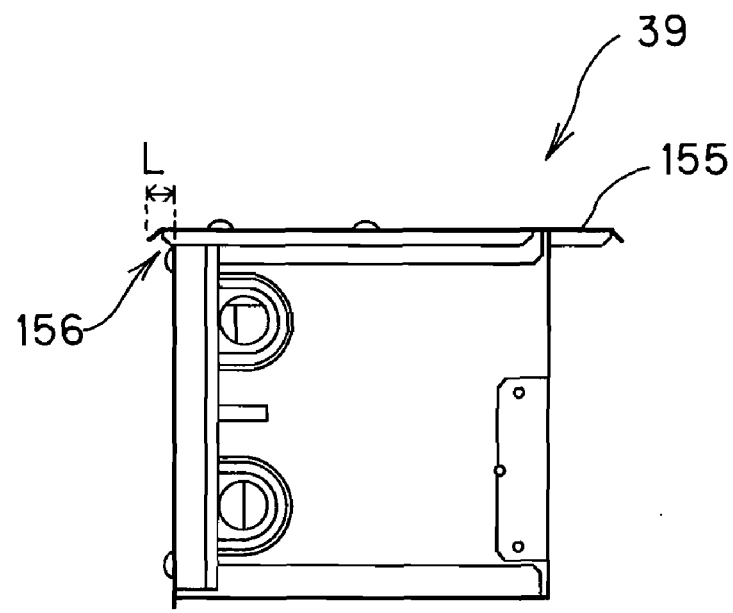
FIG. 18B is a side view of the flange portion.

As shown in FIGS. 14, 18A and 18B, a plate-shaped member 155 formed of a steel plate is fixed to the upper surface of the electrical component box 39 by screws. The plate-shaped member 155 projects to the front side of the electrical component box 39 by only a predetermined amount L, and constitutes a fringe portion 156 at the projecting portion. The water receiving tray 42, the gas-liquid contact member 53, etc. are disposed above the electrical component box 39. The fringe portion 156 projecting to the outside of the electrical component box 39 as described above prevents invasion of water, etc. into the hole 154 from the upper side of the electrical component box 39.

Figure 19A:
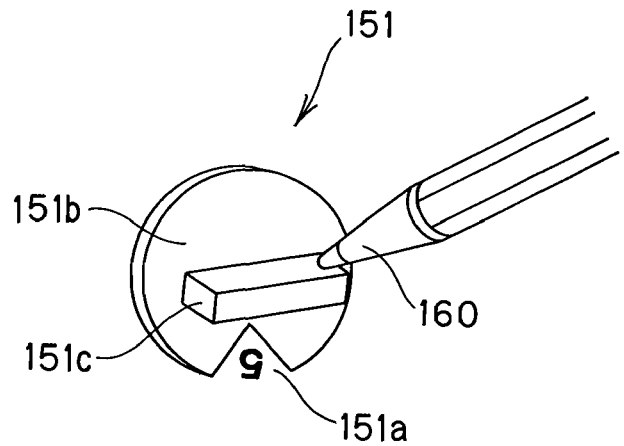
FIGS. 19A-C are diagrams showing an example of the construction of an operating unit of the electrical component box.
Figure 19B:
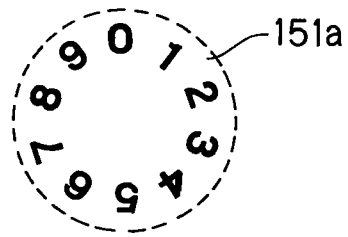
Figure 19C:
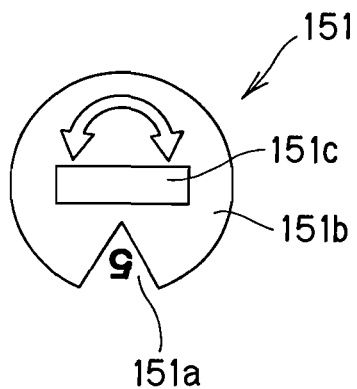

Furthermore, as shown in FIGS. 19A to 19C, the rotary operation tab 151 has a disc-shaped electrolysis condition indicating number printed (written) portion 151 on which electrolysis condition indicating numbers (power (current) state indicating numbers) of "0" to "9" are printed (written) every predetermined angle, a rotary operation portion 151b through which only one number of the electrolysis condition indicating numbers printed on the electrolysis condition indicating number printed portion 151a is exposed to the outside and the other numbers are hidden, and a tab 151 projecting from the rotary operation portion 151b. The rotary operation portion 151b may be provided so as to project from the front panel 153 of the electrical component box 39 to the outside of the electrical component box 39, or disposed to be contained in the hole 154 formed in the front panel 153 of the electrical component box 39. In this embodiment, the rotary operation tab 151 is provided so as to be contained in the hole 154 in the hole 154, and thus the tab 151 is operated by a pen point 160 or the like as shown in FIG. 19A.

In this embodiment, by rotating the rotary operation portion 151b every predetermined angle, any one of the electrolysis condition indicating numbers (power (current) supply state indicating numbers) of "0" to "9" can be selected. The controller 152 controls to supply a predetermined current value between the electrodes 47 and 48 for a predetermined current supply time so as to establish the current supply state corresponding to the electrolysis condition indicating number selected by the rotary operation tab 151.

Specifically, a predetermined power (current) supply state is associated with each electrolysis condition indicating number, and as the electrolysis condition indicating number increases, the power amount supplied to the electrodes 47, 48 is stepwise increased. At the shipping time, for example, the electrolytic condition indicating number is set to the intermediate number "5", and the electrolytic condition indicating number is freely changed in accordance with the water quality of tap water such as the concentration of ion species of water to be used for electrolysis in a district where the air filtering apparatus 100 is set, whereby the power (current) supply state between the electrodes 47 and 48 is changed.

In order to increase/reduce the power amount supplied to the electrodes 47 and 48, the current value flowing between the electrodes 47 and 48 may be increased/reduced, or the power (current) supply time between the electrodes 47 and 48 may be increased/reduced.

Furthermore, for example, some of the electrolysis condition indicating numbers may be associated with the power supply amount which is stepwise changed in accordance with these numbers as described above, and the other numbers may be associated with predetermined power (current) supply states in special operation modes, for example. These special operation modes contain a scale removing operation mode in which the power (current) is supplied between the electrodes 47 and 48 while the polarities of the electrodes 47 and 48 are inverted to remove scale, etc. deposited on the electrodes 47 and 48, a cleaning mode in which electrolytic water containing active oxygen species of a higher concentration than that under a normal state is generated and supplied to the gas-liquid contact member 53, etc. to clean the gas-liquid contact member 53, etc.

According to this embodiment, the air flow passage directing from the air suction ports 12 and 15 to the air blow-out port 13 is formed in the housing 11 by the air blower 33, and air is brought into contact with electrolytic water in the gas-liquid contact member 53 disposed on the air flow passage, whereby virus, etc. contained in sucked indoor air is filtered (inactivated, decomposed, sterilized or the like). The electrolytic bath 46 contains at least a pair of electrodes 47 and 48, and predetermined water is electrolyzed to generate electrolytic water. The power (current) supply state between the electrodes 47 and 48 of the electrolytic bath 46 is controlled by the controller 152. At this time, the rotary operation tab 151 for changing the power (current) supply state is provided to the controller 152, and the rotary operation tab 151 is exposed to the outside of the electrical component box 39 through the hole provided in the electrical component box 39 for accommodating the controller 152. Therefore, the power (current) supply state in the electrolysis process can be easily changed without opening the electrical component box 39. Furthermore, the electrical component box 39 is disposed in the housing 11, and thus the power (current) supply state between the electrodes can be prevented from being carelessly changed by the user or the like.

Furthermore, by rotating the rotary operation tab 151, the user or the like can easily stepwise change the power (current) supply state to any one of power (current) supply states of plural stages.

Furthermore, the electrical component box 39 is disposed in the housing 11 so that the rotary operation tab 151 is exposed to the outside by detaching the upper front panel 18 from the housing 11. Therefore, by detaching the upper front panel 18, the rotary operation tab 151 can be easily operated and the power (current) supply state between the electrodes 47 and 48 can be changed. Furthermore, the electrical component box 39 is accommodated in the upper front panel 18, whereby the rotary operation tab 151 is prevented from being exposed to the outside of the housing 11, and the power (current) supply state between the electrodes 47 and 48 can be prevented from being carelessly changed by the user or the like. Furthermore, the rotary operation tab 151 is contained in the hole formed in the front panel 153 of the electrical component box 39, and thus it can be prevented from being carelessly operated by the user or the like.

The present invention is not limited to the above embodiments, and various modifications may be made without departing from the subject matter of the present invention.

For example, in the above embodiments, the air filtering apparatus 100 has an on-floor mount type housing 11. However, the set style of the air filtering apparatus 100 is not limited to the on-floor mount type, and it may be a wall-suspended type, a ceiling suspended type, or an in-ceiling embedded (cassette) type, that is, it is not limited to a special style.

Still furthermore, the electrical component box 39 is disposed in the housing 11 so that the rotary operation tab 151 is exposed to the outside when the upper front panel 18 is detached from the housing 11. However, the electrical component box 39 may be disposed so that the rotary operation tab 151 is exposed to the outside when the lower front panel 19 is detached, for example. In short, the position of the electrical component box 39 is not limited to a special one insofar as the electrical component box 39 is disposed inside a face panel which is designed to be freely detachable or freely opened/closed so that the rotary operation tab 151 is exposed to the outside when the face panel is opened or detached.

What is claimed is:

1. An air filtering apparatus for generating electrolytic water, infiltrating the electrolytic water into a gas-liquid contact member, and blowing air to the gas-liquid contact member by an air blowing fan, thereby filtering air, comprising:
   a partition plate for partitioning the inside of a housing into upper and lower chambers,
   a drain pipe for discharging the electrolytic water passed through the gas-liquid contact member;
   a drain tank that has a vertical tank body receiving and stocking the electrolytic water discharged from the drain pipe; and
   a filter for collecting particles in the air which are mounted in the housing, wherein
   the gas-liquid contact member is disposed in the upper chamber,
   the air blowing fan is disposed in the lower chamber,
   the filter is disposed at the front side of the air blowing fan,
   the drain tank is disposed in juxtaposition with the air blowing fan so as to be taken in and out through the front surface of the housing,
   wherein the drain tank is provided with a grip portion which is swingably secured to the tank body, and the grip portion is movable within the swingable range so that the grip portion can be located at least in front of the tank body and at the upper side of the tank body, and
   wherein the tank body is provided with a lid having a drain port so that water in the tank body can be discharged from the drain port, and the grip portion is equipped with a closing member for closing the drain port under the state that the grip portion is located at one end of the swingable range.

2. The air filtering apparatus according to claim 1, wherein the lid is provided with a drain receiver for receiving water dropped from the drain pipe and leading the water into the tank body.

3. An air filtering apparatus comprising:
   a gas-liquid contact member provided in a housing so as to be erected in the housing,
   an electrolytic water generating unit for generating electrolytic water supplied to the gas-liquid contact member, and
   an air blowing fan for blowing air to the gas-liquid contact member,
   wherein an air flow passage for guiding air blown out from the air blowing fan to the gas-liquid contact member is formed in the housing,
   wherein the air flow passage guides the air blown out upwardly from the air blowing fan disposed at the lower side of the gas-liquid contact member to the gas-liquid contact member,
   a suppress member for suppressing an air flow amount at a side of the gas-liquid contact member which is farther from the air blowing fan is disposed in the air flow passage and
   the suppressing member is configured to suppress the air flow amount at the upper portion of the gas-liquid contact member in the air flow passage.

4. The air filtering apparatus according to claim 3, wherein the suppressing member is located in the air flow passage so as to face the upper portion of the gas-contact member.

5. The air filtering apparatus according to claim 3, wherein the suppressing member has a first low dividing plate disposed so as to face the upper end portion of the gas-liquid contact member and a second flow dividing late disposed at a lower position than the first flow dividing plate, and the first and second flow dividing plates are disposed so as to be inclined downwardly to the gas-liquid contact member.

* * * * *